United States Patent
Zhang et al.

(10) Patent No.: US 11,879,152 B2
(45) Date of Patent: Jan. 23, 2024

(54) STOICHIOMETRIC TUNING OF NUCLEIC ACID HYBRIDIZATION PROBES BY AUXILIARY OLIGONUCLEOTIDE SPECIES

(71) Applicant: William Marsh Rice University, Houston, TX (US)

(72) Inventors: David Yu Zhang, Houston, TX (US); Ruojia Wu, Houston, TX (US); Juexiao Wang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 141 days.

(21) Appl. No.: 17/168,508

(22) Filed: Feb. 5, 2021

(65) Prior Publication Data

US 2021/0164026 A1  Jun. 3, 2021

Related U.S. Application Data

(63) Continuation of application No. 15/784,855, filed on Oct. 16, 2017, now abandoned, which is a continuation of application No. PCT/US2016/027810, filed on Apr. 15, 2016.

(60) Provisional application No. 62/148,555, filed on Apr. 16, 2015.

(51) Int. Cl.
| | |
|---|---|
| *C12Q 1/68* | (2018.01) |
| *C07H 21/02* | (2006.01) |
| *C12Q 1/6832* | (2018.01) |
| *C12Q 1/6811* | (2018.01) |
| *C07H 21/04* | (2006.01) |
| *C07H 1/06* | (2006.01) |
| *C12Q 1/6876* | (2018.01) |
| *G01N 33/00* | (2006.01) |

(52) U.S. Cl.
CPC ............. *C12Q 1/6832* (2013.01); *C07H 1/06* (2013.01); *C07H 21/02* (2013.01); *C07H 21/04* (2013.01); *C12Q 1/6811* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 5,939,253 A | 8/1999 | Scholl et al. | |
| 6,444,661 B1 | 9/2002 | Barton et al. | |
| 2001/0053519 A1* | 12/2001 | Fodor | B82Y 30/00 536/24.1 |
| 2006/0051809 A1 | 3/2006 | Nazarenko et al. | |
| 2009/0111712 A1* | 4/2009 | Van Den Boom | C12Q 1/6883 536/24.3 |
| 2010/0021901 A1* | 1/2010 | Yin | C12Q 1/6818 435/6.12 |
| 2011/0009294 A1 | 1/2011 | Jones et al. | |
| 2011/0126317 A1 | 5/2011 | Vainstein et al. | |
| 2011/0306758 A1 | 12/2011 | Zhang | |
| 2012/0214686 A1 | 8/2012 | Scaboo et al. | |
| 2013/0071839 A1 | 3/2013 | Seelig et al. | |
| 2013/0274135 A1 | 10/2013 | Zhang et al. | |
| 2014/0087954 A1 | 3/2014 | Seligmann et al. | |
| 2014/0302486 A1 | 10/2014 | Seelig et al. | |

FOREIGN PATENT DOCUMENTS

| | | |
|---|---|---|
| CN | 101351564 | 1/2009 |
| CN | 103328654 | 9/2013 |
| CN | 103649335 | 3/2014 |
| CN | 104093857 | 10/2014 |
| WO | WO 2006/097854 | 9/2006 |
| WO | WO 2012/058488 | 5/2012 |
| WO | WO 2014/041024 | 3/2014 |
| WO | WO 2015/094429 | 6/2015 |

OTHER PUBLICATIONS

"Fungi," Wikipedia.com, accessed Jun. 3, 2013.
"How many species of bacteria are there," Wisegeek.com, accessed Jan. 21, 2014.
"List of sequenced bacterial genomes," Wikipedia.com, accessed Jan. 24, 2014.
"Mammal," Wikipedia.com, accessed Sep. 22, 2011.
"Murinae," Wikipedia.com, accessed Mar. 18, 2013.
"Oligonucleotide definition," Merriam-Webster.com, accessed Aug. 23, 2017.
"Viruses," Wikipedia.com, accessed Nov. 24, 2012.
Begley, "Psst, the human genome was never completely sequenced," *STAT News*, 2017.
Duncavage et al., "Hybrid capture and next0generation sequencing identify viral integration sites from formalin-fixed, paraffin-embedded tisse," *J Mol Diagn.*, 13:325-333, 2011.
European Search Report issued in EP Application No. 16780863, dated Dec. 13, 2018.
Forster et al., "A human gut bacterial genome and culture collection for improved metagenomic analyses," *Nature Biotechnology*, 37:186-192, 2019.
Li et al., "A new class of homogenous nucleic acid probes based on specific displacement hybridization," *Nucleic Acids Research*, vol. 30, No. 2, Jan. 15, 2002.
Office Action issued in Chinese Application No. 201680034110.7, dated Aug. 5, 2020 (English language translation thereof).

(Continued)

*Primary Examiner* — Bradley L. Sisson
(74) *Attorney, Agent, or Firm* — Parker Highlander PLLC

(57) ABSTRACT

This invention describes a method of controlling the hybridization yield of nucleic acid probes by adjusting the relative concentrations of auxiliary oligonucleotides to the probes and the targets. The auxiliary oligonucleotide is partially or fully complementary to either the probe or the target, and is released upon hybridization of the probe to the target.

14 Claims, 19 Drawing Sheets

Specification includes a Sequence Listing.

(56) References Cited

OTHER PUBLICATIONS

Office Action issued in U.S. Appl. No. 15/784,855, dated Jul. 17, 2020.
Office Action issued in U.S. Appl. No. 15/784,855, dated Jun. 21, 2019.
Office Action issued in U.S. Appl. No. 15/784,855, dated May 11, 2018.
Office Action issued in U.S. Appl. No. 15/784,855, dated Nov. 6, 2020.
Office Action issued in U.S. Appl. No. 15/784,855, dated Oct. 29, 2019.
Shen et al., "Multiplex target capture with double-stranded DNA probes," *Genome Med.*, 5:50, 2013.
Wang et al., "Simulation-guided DNA probe design for consistently ultraspecific hybridization," *Nat Chem.*, 7:545-553, 2015.
Wu et al., "Continuously tunable nucleic acid hybirdization probes," *Nat Methods*, 12:1191-1196, 2015.
Zeraati et al., "I-motif DNA structures are formed in the nuclei of human cells," *Nature Chemistry*, 10:631-637, 2018.
Zhang et al., "Optimizing the specificity of nucleic acid hybridization," *Nat Chem.*, 1:208-214, 2012.
Zhang et al., "Control of DNA Strand Displacement Kinetics Using Toehold Exchange." *Journal of the American Chemical Society*, vol. 131, No. 47, Dec. 2, 2009.

\* cited by examiner

100% GC T: 5'-GGCGCCCCCGCCGGCCCCGCCGCCGCCGC-3'

0% GC T: 5'-TTATAAAAATAATTAAAATAATAATAATA-3'

STOICHIOMETRIC TUNING OF NUCLEIC ACID HYBRIDIZATION PROBES BY AUXILIARY OLIGONUCLEOTIDE SPECIES

CROSS-REFERENCE TO RELATED APPLICATIONS

The present application is a continuation of U.S. application Ser. No. 15/784,855, filed Oct. 16, 2017, which is a continuation of International Application No. PCT/US2016/27810 filed on Apr. 15, 2016 which claims the benefit of U.S. Provisional Application No. 62/148,555, filed on Apr. 16, 2015, each of which is incorporated by reference herein in its entirety.

STATEMENT OF GOVERNMENT INTEREST

This invention was made with government support under Grant Number R00EB015331 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 2, 2021, is named RICEP0064USC1.txt and is ~3 kilobytes in size.

BACKGROUND

Nucleic acids encode vast amounts of biological and clinical information, and next-generation sequencing (NGS) is a promising family of approaches to improving understanding of biology and informing healthcare decisions. The standard NGS platforms (Illumina and IonTorrent) provide roughly 10 million "reads" of subsequences up to 250 nucleotides (nt) long in a single run, for a total of roughly 2 gigabases of information.

To obtain maximum useful information from limited NGS reads, researchers and diagnostics developers utilize methods to enrich biological samples for nucleic acid sequences of interest. For example, the DNA from the white blood cells and the RNA from red blood cells contain little clinically useful information; it is the rare circulating tumor cells (CTCs), cell-free DNA in exomes (cfDNA), or sepsis-causing bacteria that can inform clinical action. Alternatively, in biopsy margin samples, researchers or clinicians may wish to enrich for the sequences of particular genes (or the exome). Currently, such "targeted" sequencing represent the dominant majority of current NGS usage.

This invention describes a method of controlling the hybridization yield of nucleic acid probes by adjusting the relative concentrations of auxiliary oligonucleotides to the probes and the targets. The auxiliary oligonucleotide is partially or fully complementary to either the probe or the target, and is released upon hybridization of the probe to the target.

Enrichment of desired sequences can come in a variety of forms, from simple sample-preparation protocols (e.g. centrifugation), to instruments for capturing specific cells based on morphology, to kits that selectively capture particular nucleic acid sequences. In this invention, enrichment will refer specifically to last class: molecular techniques that differentially interact with different nucleic acid sequences to result in an enriched sample with higher fraction of the desired set of sequences.

There are two broad approaches to molecular enrichment: hybrid-capture and multiplexed PCR. Hybrid-capture uses the specificity of Watson-Crick hybridization to "capture" target nucleic acid sequences using complementary "probe" molecules; non-cognate sequences in the sample are not captured and are removed through a washing process. Multiplexed PCR uses a large number of primers to simultaneously amplify all sequences of interest via PCR (typically only 8-10 cycles); non-cognate sequences in the sample are not amplified. Currently, both methods have significant error and bias: multiplexed PCR because the polymerase enzyme intrinsically prefers certain sequences and has limited fidelity, and hybrid-capture because hybridization probe design is imperfect and results in nonspecific interactions as well as biases in capture yields. The current invention addresses bias in hybrid-capture molecular enrichment techniques.

Affinity (sensitivity) and selectivity (specificity) of nucleic acid probes/primers are inversely correlated properties; improvement of one metric generally leads to deterioration of the other. Different applications of nucleic acid probes have different requirements of sensitivity and specificity. For example, NGS target enrichment assays require high specificity capture of DNA (e.g. Illumina Nextera, Agilent SureSelect, and IDT xGen); in depletion assays, high yield (sensitivity) is desired (e.g. NEB NuGen). Additionally, highly multiplexed applications need uniform yield of different targets to minimize bias.

Current practice of probe design is usually based on bioinformatics software-predicted thermodynamic properties. However, inaccuracies of up to 3 kcal/mol of reaction energy still occur due to imperfect biophysics model and literature parameters, especially in a multiplexed setting. Empirical adjustments of operating conditions and probe sequences are usually used to compensate for the inaccuracy in probe design; but these methods are expensive and time-consuming, and often lack precision.

SUMMARY

The present disclosure provides methods for stoichiometric tuning of hybridization probes using competitive auxiliary nucleic acid species. These methods are broadly classified into designs wherein the auxiliary species is complementary to the target (blockers) and designs wherein the auxiliary species is complementary to the probe (protectors). Both implementations offer on-the-fly adjustment of the hybridization yield, provide more predictive and precise control than probe sequence adjustment, and allow iterative tuning for multiplexed assays and for complex target sequences.

In an embodiment, a method for providing a nucleic acid probe for selective capture or enrichment of a nucleic acid molecule bearing a target nucleic acid sequence with a desired yield is provided, the method comprising contacting a first sample containing the nucleic acid molecule bearing the target nucleic acid sequence with a test solution comprising the nucleic acid probe at a temperature and a buffer condition conducive to hybridization of the target nucleic acid sequence to the nucleic acid probe. The nucleic acid probe includes a first nucleic acid molecule and a second nucleic acid molecule. The first and second nucleic acid molecules are present in the nucleic acid probe at a first concentration and a second concentration, respectively, and the second concentration is greater than the first concentration. The first nucleic acid sequence includes a first probe subsequence and a second probe subsequence which are complementary to a first target subsequence and a second target subsequence of the nucleic acid molecule, respectively. The second nucleic acid sequence includes a third probe subsequence that is complementary to at least a subsequence of the first probe subsequence. The method then includes a step for determining an experimental yield, the experimental yield being the proportion of the target nucleic acid sequence that is hybridized to the first nucleic acid molecule. Once the experimental yield is determined, a third concentration $[P]'_0$ of the second nucleic acid molecule is determined according to Equation 1, where $[P]_0$ is the second concentration, $\chi_1$ is the experimental yield and $\chi_2$ is the desired yield which is the desired proportion of the target nucleic acid sequence that is hybridized to the first nucleic acid molecule. Once the third concentration is determined, the method further includes the step of providing instructions to use the third concentration of the second nucleic acid molecule for preparation of the nucleic acid probe or preparing the nucleic acid probe with the second nucleic acid molecule at the third concentration.

In another embodiment, a method for providing a nucleic acid probe for selective capture or enrichment of a nucleic acid molecule bearing a target nucleic acid sequence with a desired yield is provided, the method comprising contacting a first sample containing the nucleic acid molecule bearing the target nucleic acid sequence with a test solution comprising the nucleic acid probe at a temperature and a buffer condition conducive to hybridization of the target nucleic acid sequence to the nucleic acid probe. The nucleic acid probe includes a first nucleic acid molecule and a second nucleic acid molecule. The first and second nucleic acid molecules are present in the nucleic acid probe at a first concentration and a second concentration, respectively. The first nucleic acid sequence includes a first probe subsequence and a second probe subsequence which are complementary to a first target subsequence and a second target subsequence of the nucleic acid molecule, respectively. The first target subsequence includes at least a portion of the target nucleic acid sequence. The second nucleic acid sequence includes a third probe subsequence that is complementary to the first target subsequence. The second nucleic acid molecule does not contain a subsequence that is complementary to the second target subsequence. The method then includes a step for determining an experimental yield, the experimental yield being the proportion of the target nucleic acid sequence that is hybridized to the first nucleic acid molecule. Once the experimental yield is determined, a third concentration $[B]'_0$ of the second nucleic acid molecule is determined according to Equation 2, where $[B]_0$ is the second concentration, $\chi_1$ is the experimental yield and $\chi_2$ is the desired yield which is the desired proportion of the target nucleic acid sequence that is hybridized to the first nucleic acid molecule. Once the third concentration is determined, the method further includes the step of providing instructions to use the third concentration of the second nucleic acid molecule for preparation of the nucleic acid probe or preparing the nucleic acid probe with the second nucleic acid molecule at the third concentration.

In still another embodiment, a nucleic acid probe composition for selectively capturing or enriching a nucleic acid molecule bearing a target nucleic acid sequence is provided. The nucleic acid probe composition includes a first nucleic acid molecule and a second nucleic acid molecule at a first concentration and a second concentration, respectively. The first nucleic acid molecule includes a first probe subsequence that is complementary to a first target subsequence of the nucleic acid molecule and a second probe subsequence that is complementary to a second target subsequence of the nucleic acid molecule. The first target subsequence includes at least a portion of the target nucleic acid sequence. The second nucleic acid molecule includes a third probe subsequence and a fourth probe subsequence. The third probe subsequence is complementary to the first target subsequence or a subsequence contained within the first target subsequence. The fourth probe subsequence is complementary to a third target subsequence that is separate from the first and second target subsequences, but is within 30 nucleotides of the first or second target subsequences.

DRAWINGS

FIG. 1A depicts an example embodiment of the Protector (PC) implementation. The first nucleic acid molecule is referred to as C, and may be functionalized to allow capture or detection. Yield is calculated as the fraction of target T bound to C. C comprises a second region (denoted as "2"), a first region (denoted as "1"), and a fourth region (denoted as "4"). The second nucleic acid molecule is referred to as the Protector P, which comprises the fifth region (denoted as "5") and the third region (denoted as "3"). Here the third region is complementary to the first region, and the fifth region is complementary to the fourth region. P is released upon hybridization of PC to the target T. P is in higher concentration than C, and the yield is adjusted by initial P concentration.

FIG. 1B depicts an example embodiment of the Blocker (BD) implementation. The first nucleic acid molecule is referred to as D, and may be functionalized to allow capture or detection. Yield is calculated as the fraction of target bound to D. D comprises a second region (denoted as "7") and a first region (denoted as "6"). The second nucleic acid molecule is referred to as the Blocker B, which comprises a fourth region (denoted as "9") and a third region (denoted as "8"). Here the third region is identical in sequence to the second region. When B and D are added to a sample containing T, T is more likely to initially hybridize to B due to its higher concentration than D; then hybridization of TB to D releases B. The yield is adjusted by initial B concentration.

FIG. 2A depicts the nucleic acid sequences of T, P, C (SEQ ID NOS 1-3, respectively) and the intended reaction for an experimental demonstration of the Protector implementation. The arrangement of subsequences on P and C is shown in FIG. 1a. C is modified by a TAMRA fluorophore on 3' end, and P by an Iowa Black® RQ quencher on 5' end. The release of P results in an increase in fluorescence.

FIG. 2B depicts the experimental results of stoichiometric tuning. Each data point shows the mean observed fluorescence and corresponding yield at a particular $[P]_0/[PC]_0$ value (n=3), and the error bar shows ±1 standard deviation. The black sigmoidal curve shows the predicted (analytical) yield based on the best-fit reaction $\Delta G°=-2.15$ kcal/mol. Inset shows zoom-in of 6 sets of experiments with $[P]_0/[PC]_0$ spaced by $10^{0.02}$(4.7%). All experiments were performed in triplicate at 1×PBS at 25° C., $[PC]_0$=100 pM, and $[T]_0$=200 pM.

FIG. 3A depicts the target reaction with X-probe. 31 distinct probes were designed to target 31 DNA targets with G/C content ranging from 0% to 100%.

FIG. 3B depicts stoichiometric tuning for capture uniformity of observed yields for probes and exemplary sequences having 100% and 0% G-C content (SEQ ID NOS 4-5, respectively, in order of appearance) with corresponding targets at $[P]_0/[C]_0=3$ (Before Tuning), after 1 round of tuning (1 Round Tuning), and after 2 rounds of tuning (2 Rounds Tuning). We were able to tighten the yield distribution from between 57.3% and 13.4% to between 37.2% and 24.0%, regardless of GC content. All experiments were performed in triplicates in 5× excess of human genomic DNA (100 ng) at 5×PBS with 0.1% Tween 20 at 37° C.

Figure 4A:
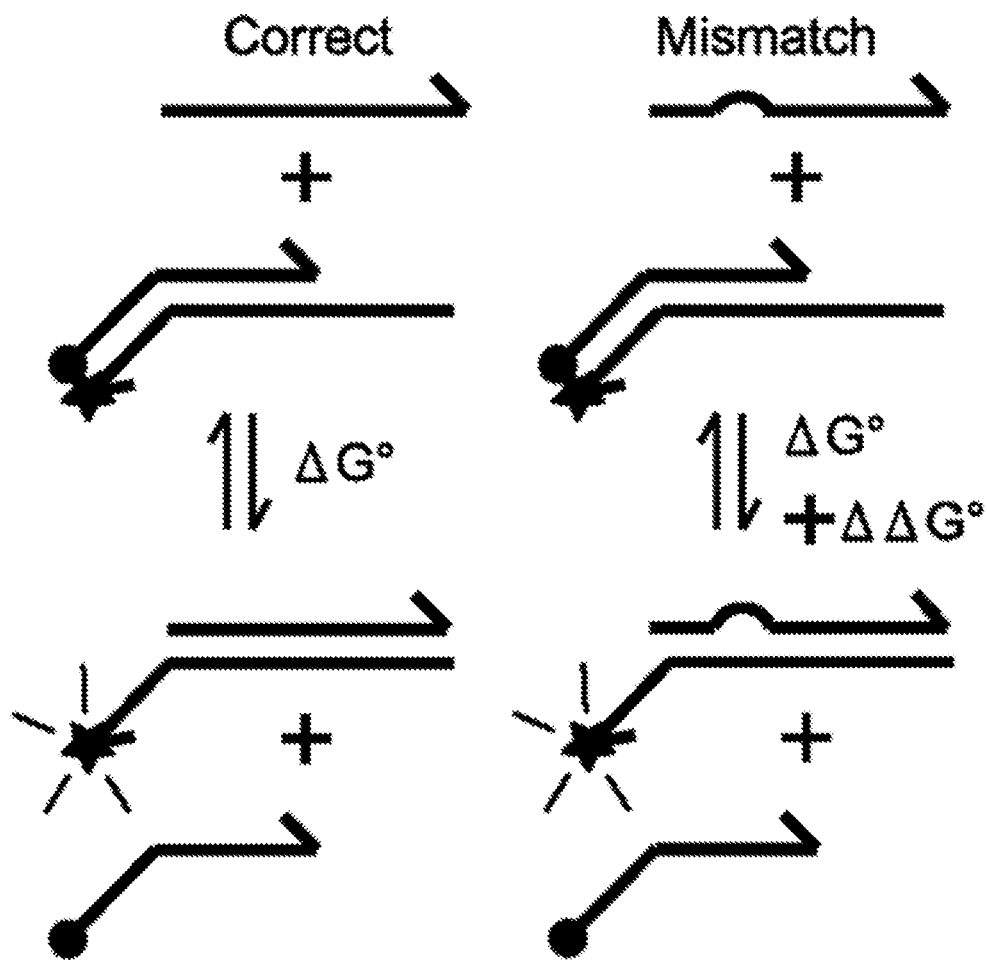
FIG. 4A depicts the difference in binding yield between two SNP variants results from the ΔG° of their respective hybridization to a probe.
Figure 4B:
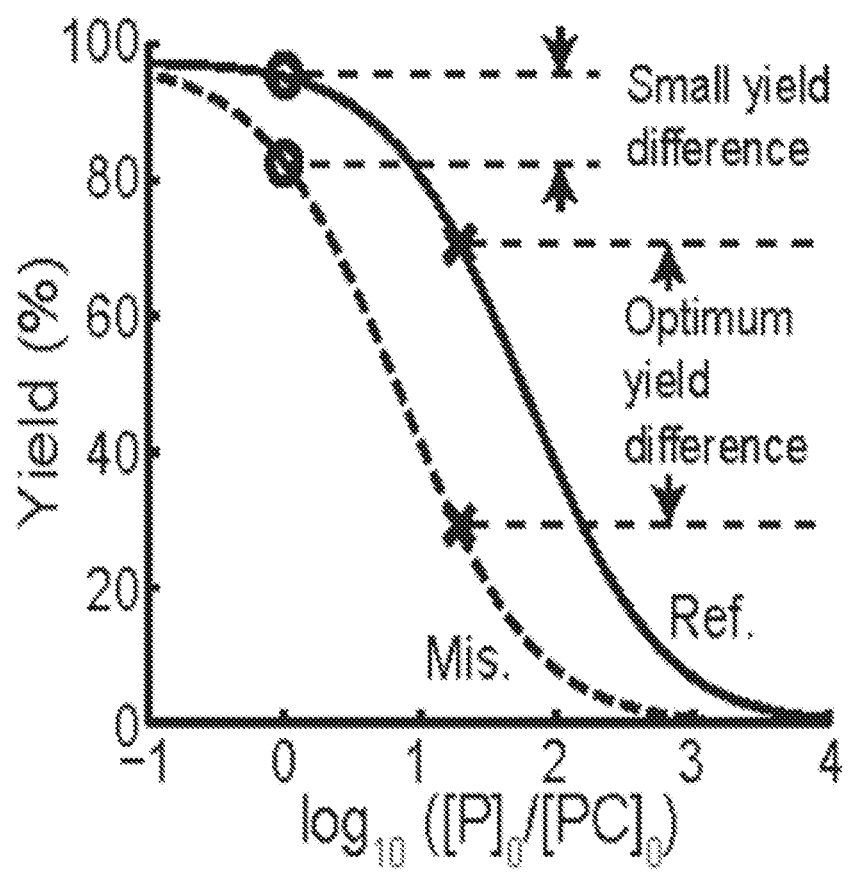
FIG. 4B depicts a theoretical graph showing that the same ΔG° value produces different yield differences based on the value of $[P]_0/[PC]_0$.
Figure 4C:
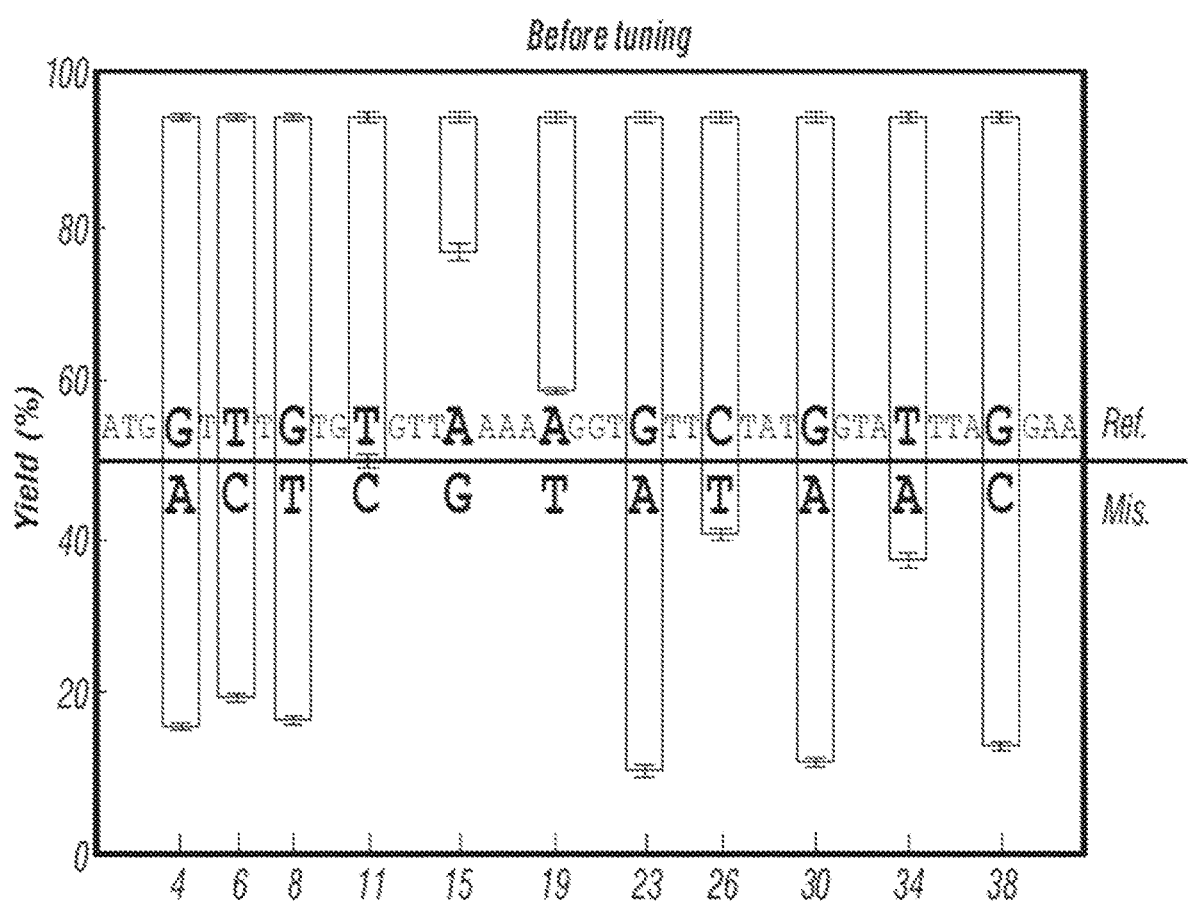
FIG. 4C depicts the observed yields for intended target (top edge of bars) and 11 single nucleotide variants (bottom edges of bars), at $[P]_0/[PC]_0=1$ (SEQ ID NO: 6). All experiments were performed in triplicate at 1×PBS at 37° C., $[PC]_0=100$ nM, and $[T]_0=200$ nM.
Figure 4D:
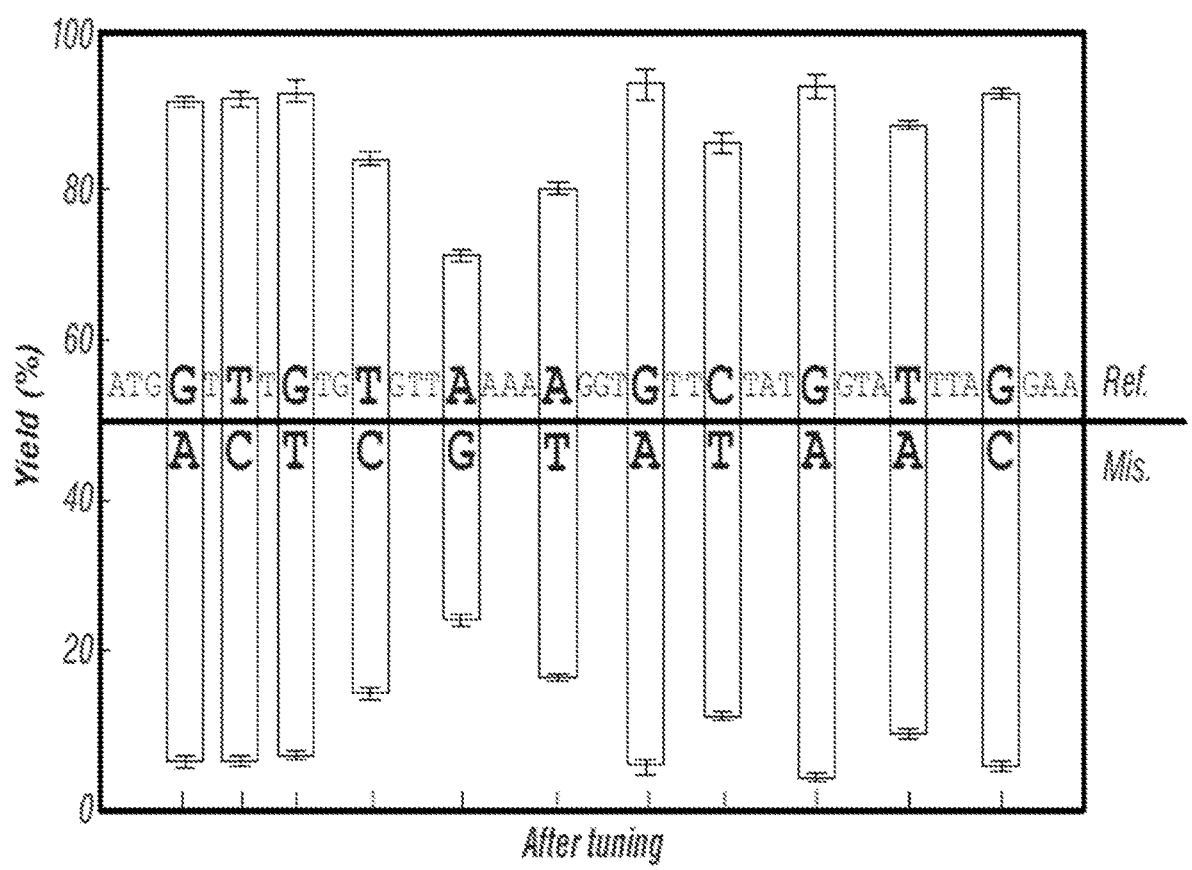

FIG. 4D depicts the yields after stoichiometric tuning (SEQ ID NO: 6). Different $[P]_0/[PC]_0$ ranging from 3.74 to 29.5 were used for each SNP pair. The range of yield difference was improved from 17.2-83.3% to 47.0-88.6% through the course of stoichiometric tuning.

Figure 1A:
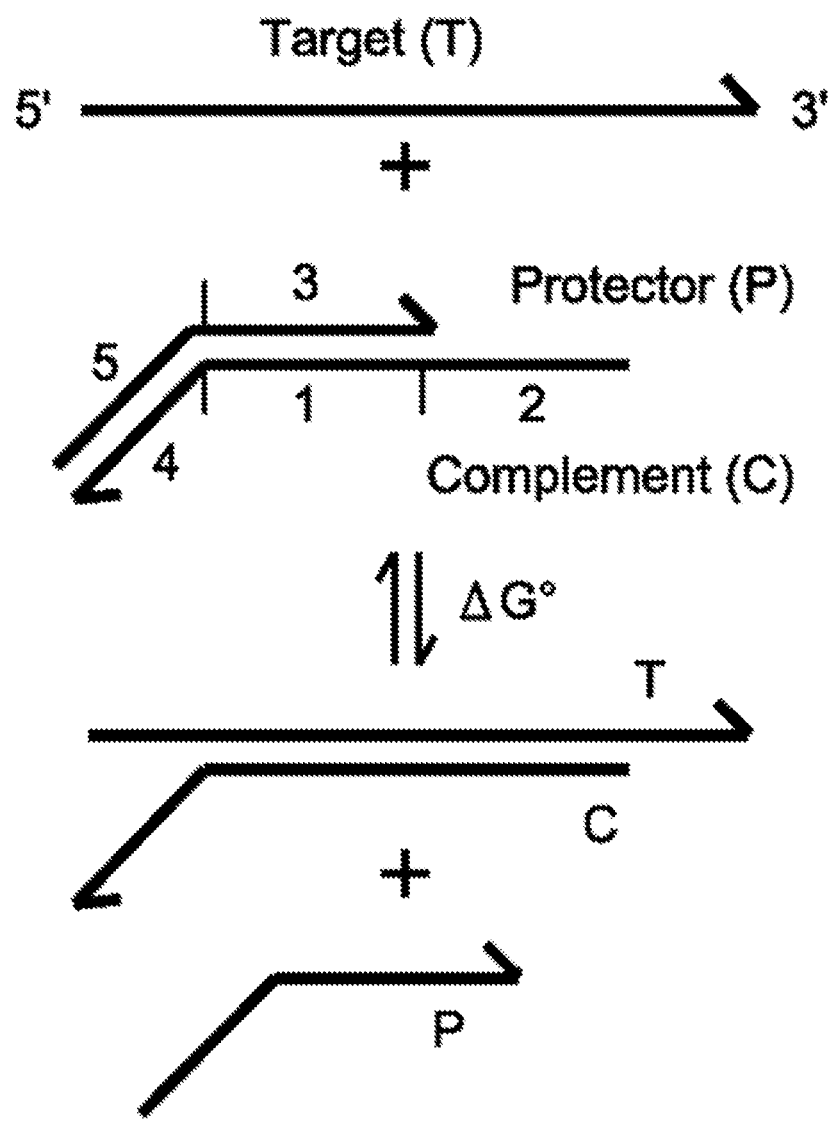
Figure 1B:
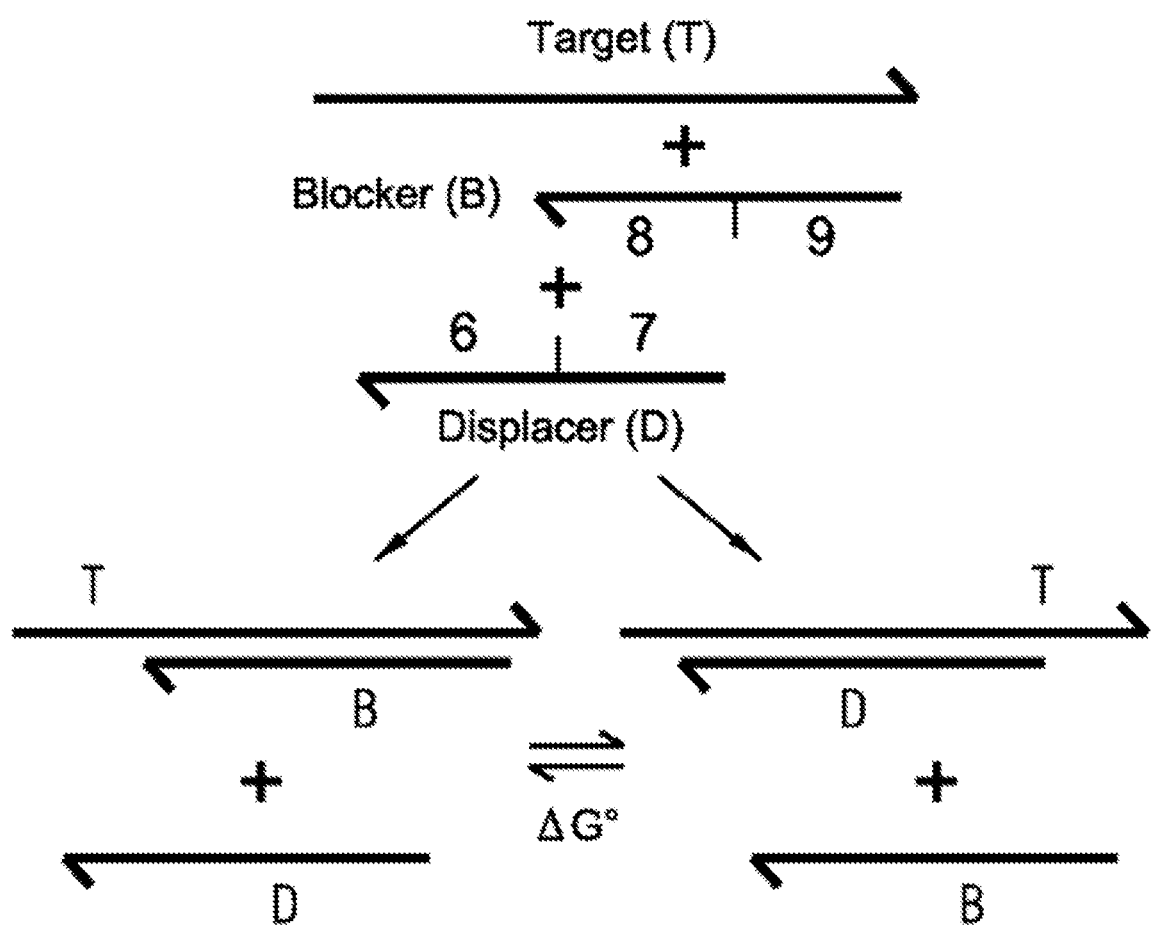
Figure 5A:
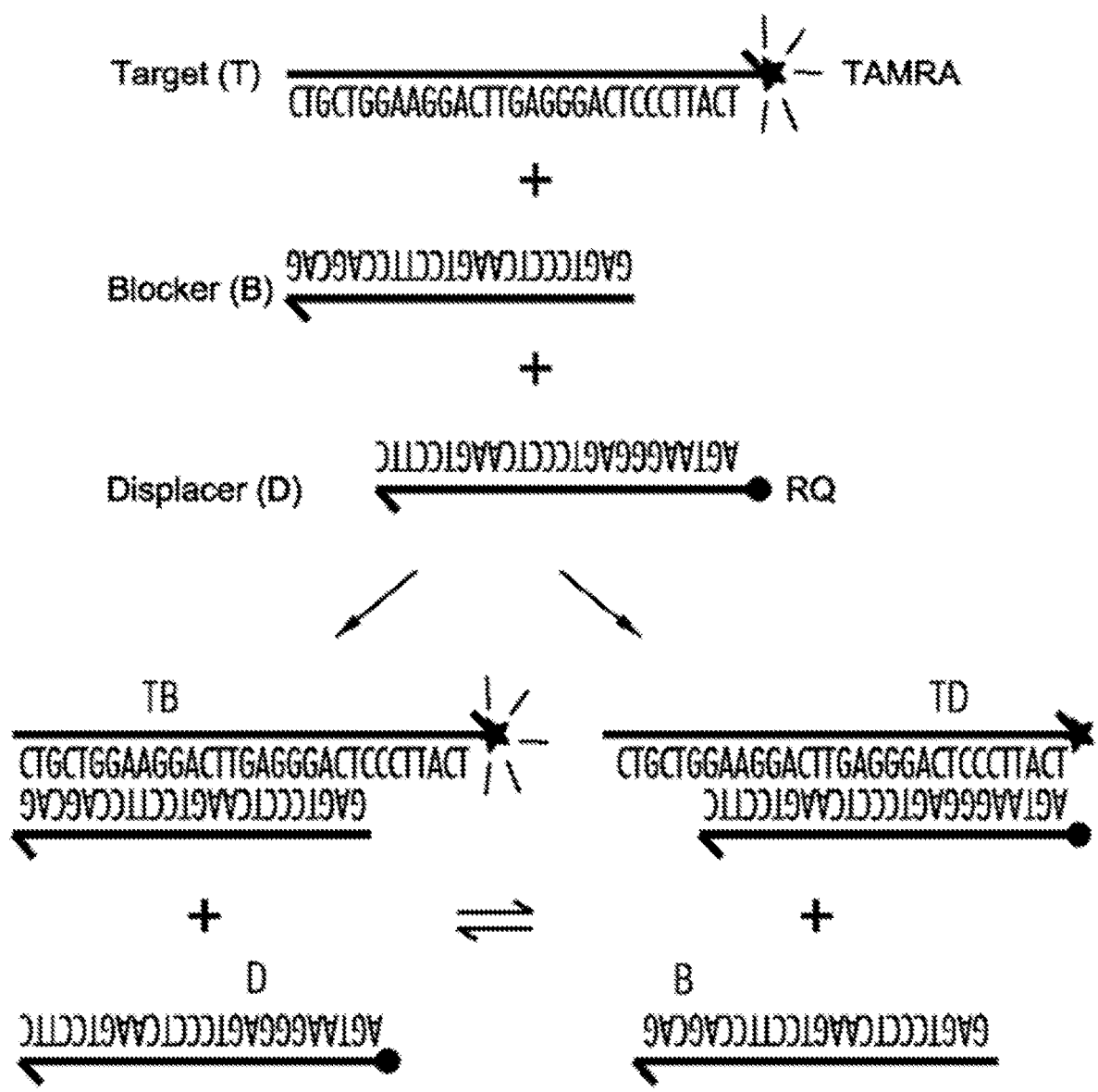

FIG. 5A depicts a scheme for an example demonstration of the BD implementation including the nucleic acid sequences of T, B, D (SEQ ID NOS 7-9, respectively) and the intended reaction. The arrangement of subsequences on B and D is shown in FIG. 1B. T is modified by a TAMRA fluorophore on 3' end, and D by an Iowa Black® RQ quencher on 5' end. The hybridization between T and D results in a decrease in fluorescence.

Figure 5B:
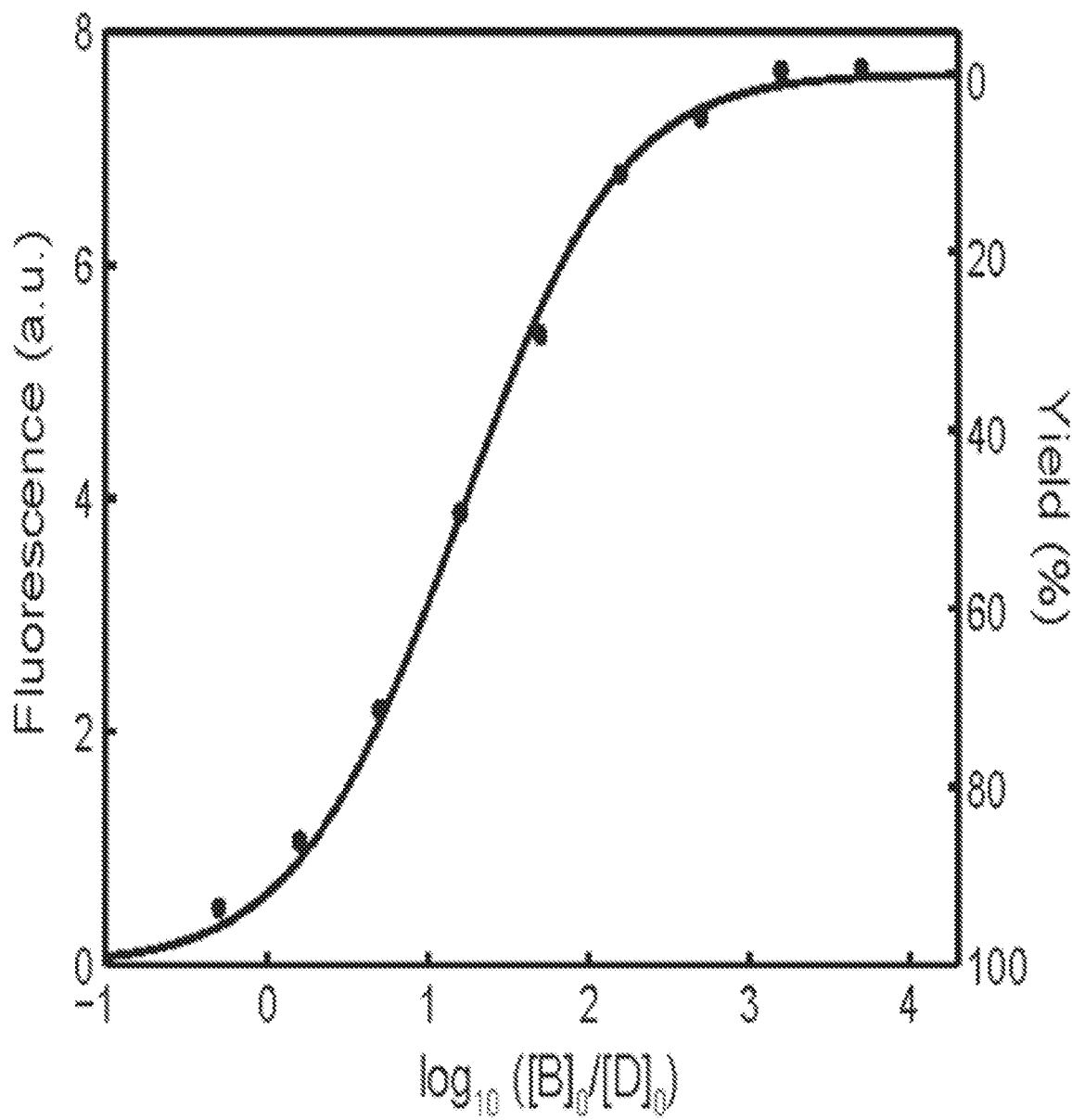

FIG. 5B depicts the experimental results of stoichiometric tuning according to the scheme in FIG. 5A. Each data point shows the observed fluorescence and corresponding yield at a particular $[B]_0/[D]_0$ value. The black sigmoidal curve shows the predicted (analytical) yield based on the best-fit reaction ΔG°=−1.79 kcal/mol. All experiments were performed in triplicate at 1×PBS at 25° C., and $[D]_0=200$ pM.

Figure 6A:
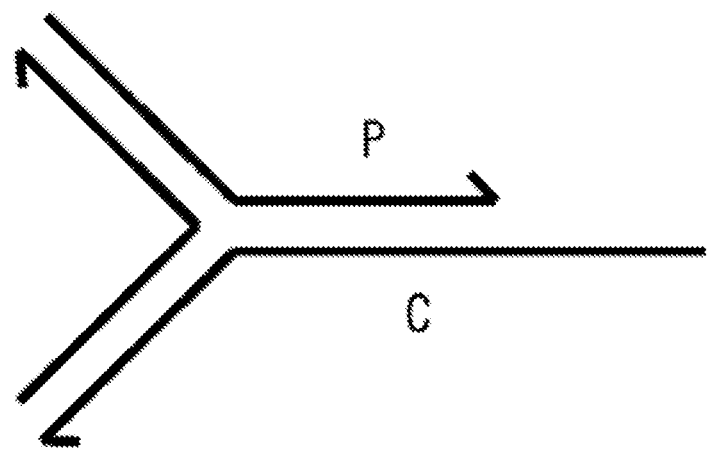

FIG. 6A depicts a variant architecture of the PC embodiment where P comprises 2 oligonucleotides, which are bound together by an additional region.

Figure 6B:
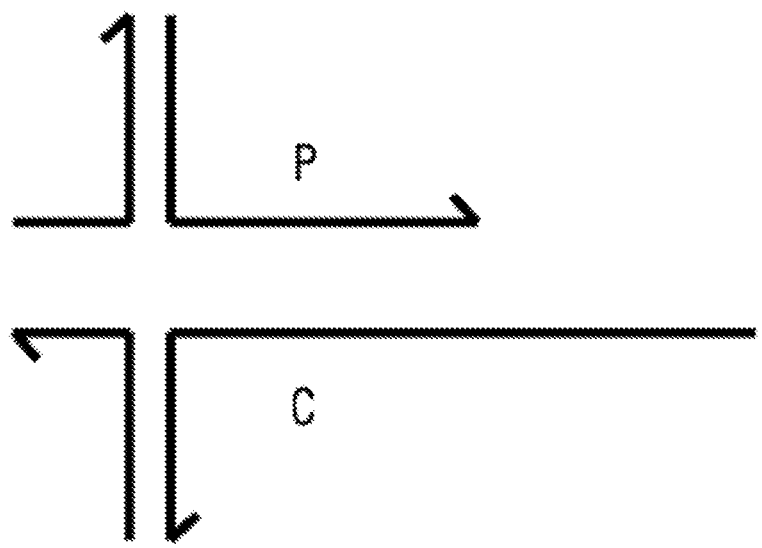

FIG. 6B depicts a variant architecture of the PC embodiment known as X-probe architecture. P and C both comprise 2 oligonucleotides.

Figure 6C:
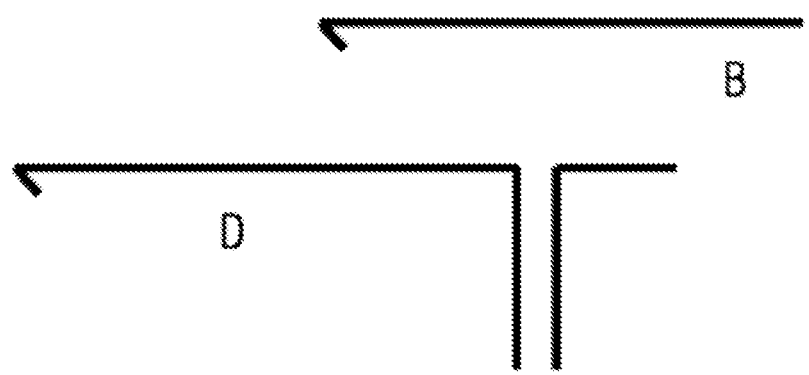

FIG. 6C depicts a variant architecture of the BD embodiment where D comprises 2 pre-hybridized oligonucleotides.

Figure 6D:
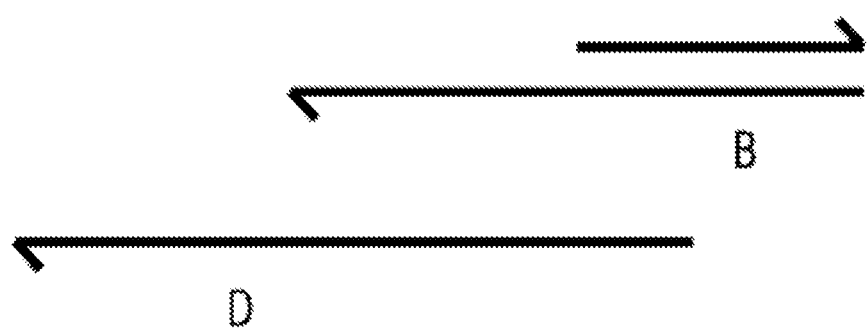

FIG. 6D depicts a variant architecture of the BD embodiment where B comprises an additional complementary strand which is release upon hybridization of B to the target.

Figure 7A:
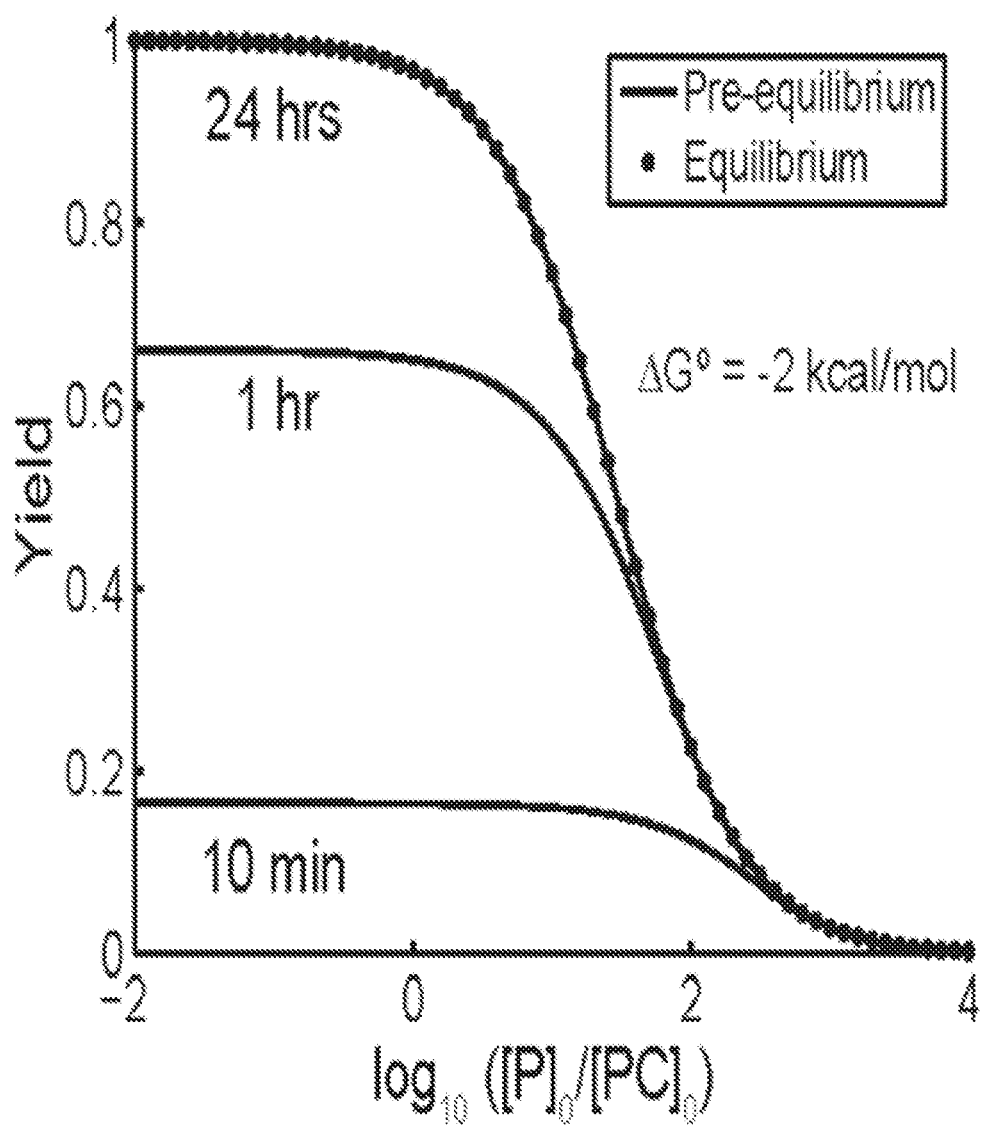

FIG. 7A depicts the simulated yield at different reaction times for pre-equilibrium stoichiometric tuning of the PC implementation. ODE simulations of reaction PC+T⇌TC+P show that pre-equilibrium yield can be tuned by stoichiometry similarly to equilibrium yield. At pre-equilibrium conditions, the maximum achievable yield is less than 1. It was assumed that $[PC]_0=100$ pM, $[T]_0=10$ fM, $k_f=3\times10^6$ s$^{-1}$M$^{-1}$, ΔG°=−2 kcal/mol, and τ=25° C.

Figure 7B:
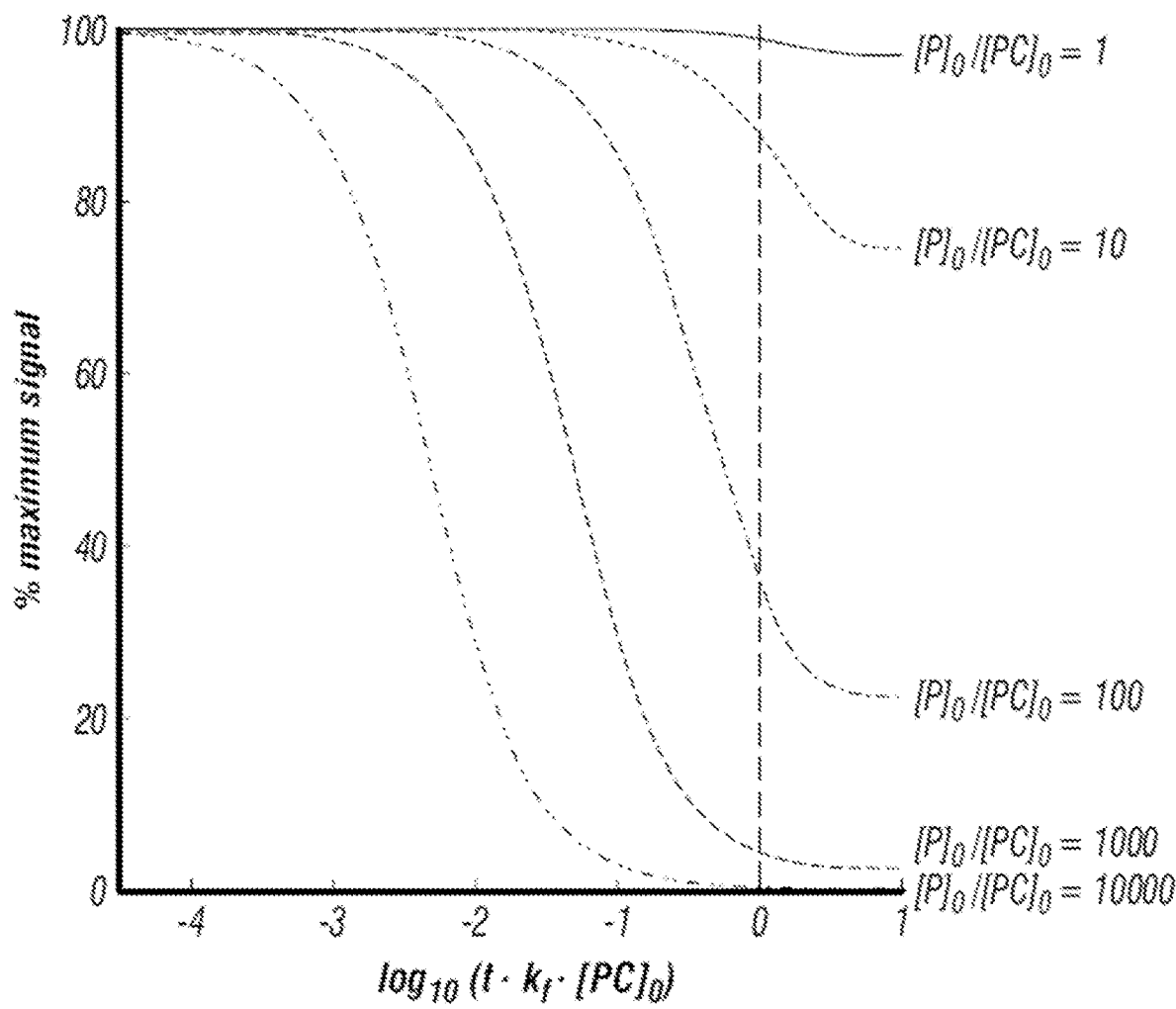

FIG. 7B depicts the % maximum signal as a function of $t \cdot k_f \cdot [PC]_0$ to establish criteria of pre-equilibrium stoichiometric tuning. The change of percentage maximum signal becomes less sensitive to stoichiometry when $t \cdot k_f \cdot [PC]_0$ becomes smaller. The criterion $t \cdot k_f \cdot [PC]_0>1$ indicates that the stoichiometric tuning can be implemented using the equilibrium method.

Figure 7C:
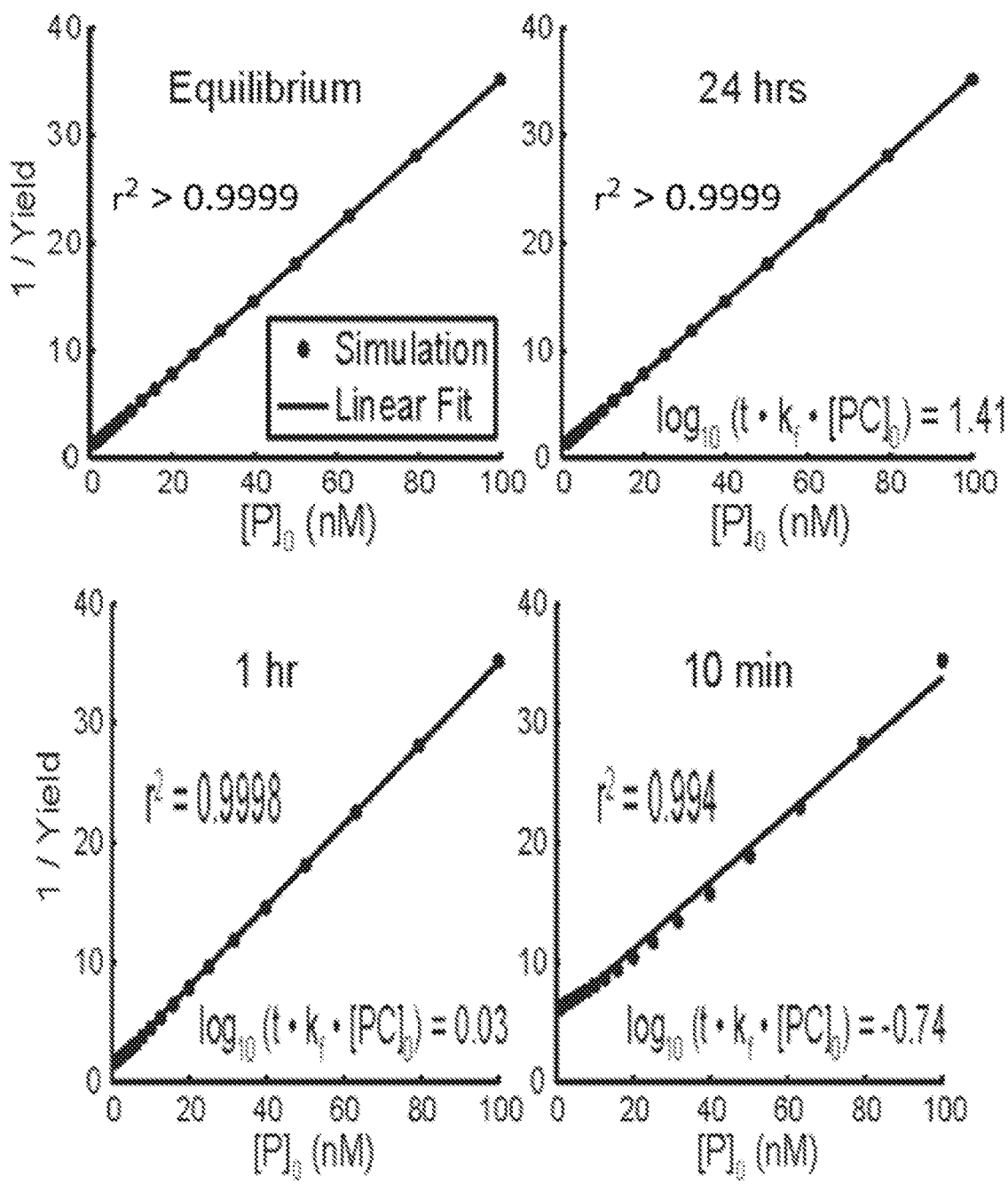

FIG. 7C depicts a linear fit of 1/χ to $[P]_0$. The reaction time lengths that satisfy $t \cdot k_f \cdot [PC]_0>1$ show high linearity ($r^2>0.999$).

Figure 8A:
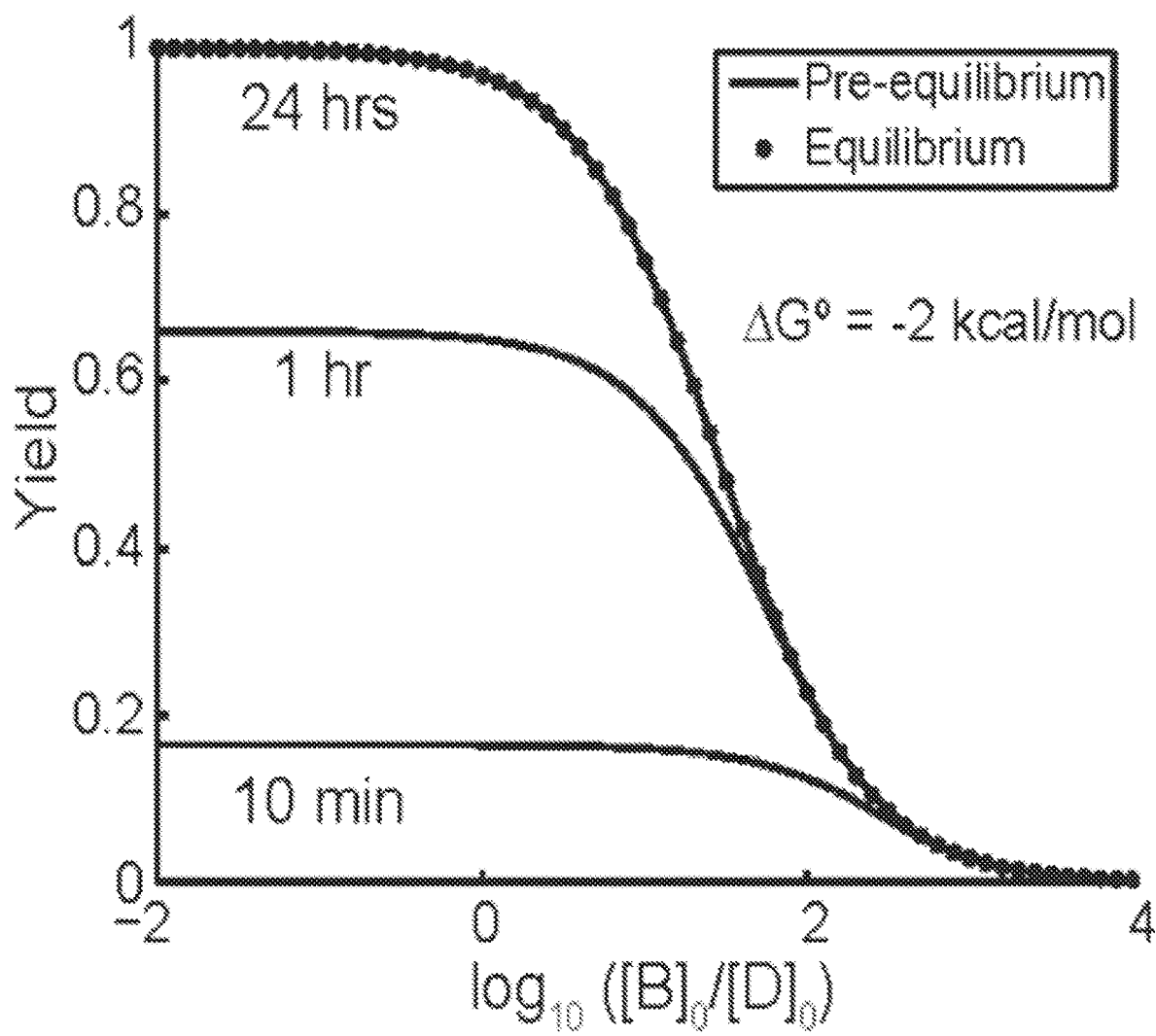

FIG. 8A depicts a simulation of pre-equilibrium stoichiometric tuning of BD implementation showing the simulated yield at different reaction times.

Figure 8B:
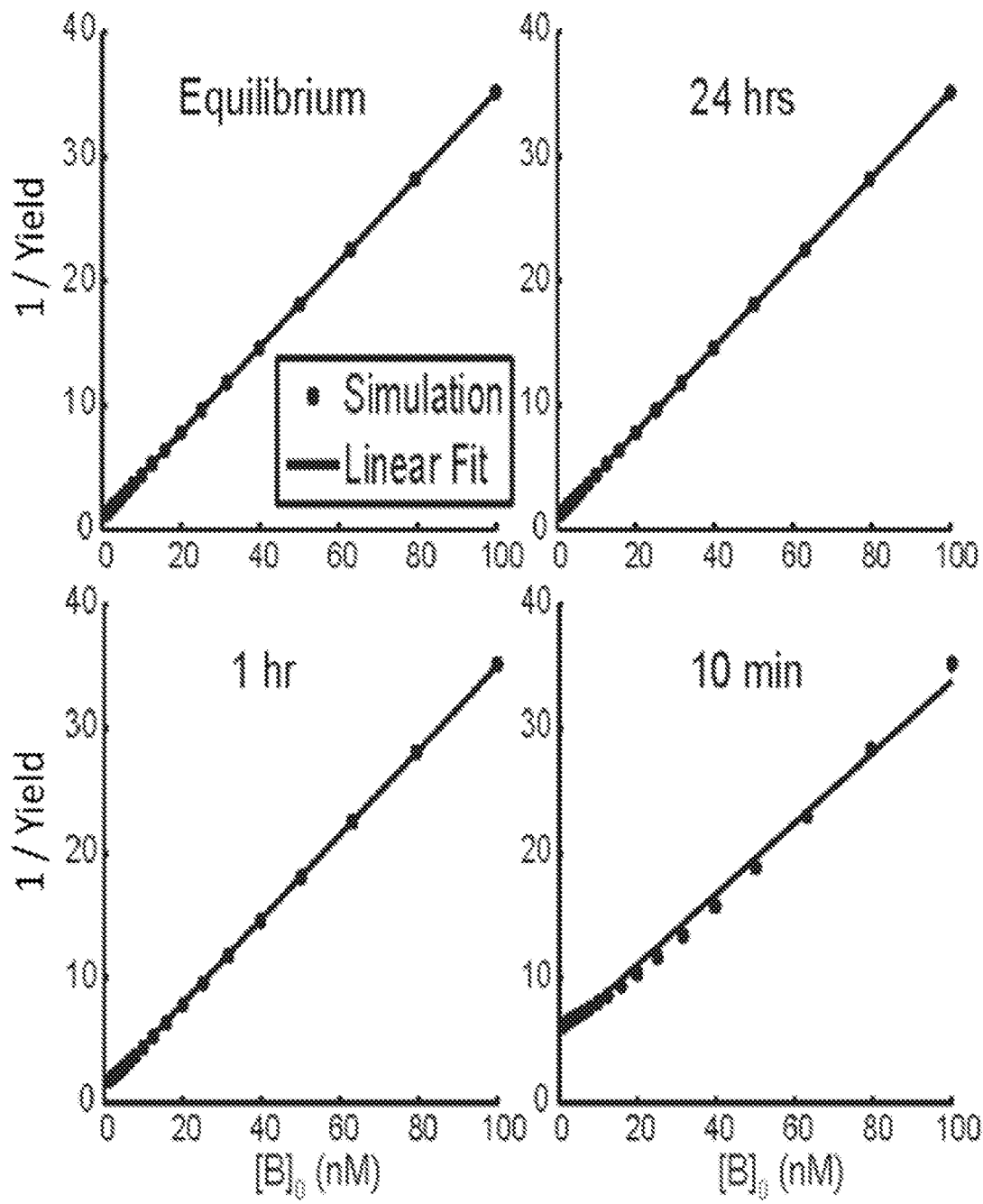

FIG. 8B depicts a linear fit of 1/χ to $[B]_0$. FIGS. 8A and 8B show similar results to FIGS. 7A and 7C. It was assumed that $[D]_0=100$ pM, $[T]_0=10$ fM, $k_f=3\times10^6$ s$^{-1}$M$^{-1}$, ΔG°=−2 kcal/mol, and τ=25° C.

DESCRIPTION

Protector Implementation:

The Protector implementation involves a probe nucleic acid molecule (denoted as C) comprising a first and a second subsequence that are complementary to adjacent subsequences of the target, and an auxiliary nucleic acid molecule (denoted as the Protector or P) comprising a third subsequence that is complementary to the first subsequence; P has higher initial concentration than C. In some embodiments, C further comprises a fourth subsequence that is not complementary to the target sequence, and P further comprises a fifth subsequence that is complementary to the fourth subsequence. In some embodiments, C and P are each an oligonucleotide, and the mixture of C and P is known as a toehold probe; an example of this embodiment is illustrated in FIG. 1A. More information on toehold probes can be found in WO 2015/094429 A1, which is incorporated herein by reference in its entirety.

As used herein, the term "subsequence" refers to a sequence of at least 5 contiguous base pairs.

The sequence design of P and C, relative to a target sequence T, are such that the preponderance of T and P molecules are mutually exclusive in hybridization to C, with only a small concentration of trimolecular intermediate species TPC existing at any given point of time. Additionally, C is designed to bind stably to both P and to T, with only a small concentration of free C existing at any given point of time when the sum of the concentrations of P and T exceed that of C. When these assumptions are met, the system can be simply expressed by the chemical reaction: PC+T⇌TC+P. The yield of this reaction at a given time t is defined as:

$$\chi_t = \frac{[TC]_t}{\min([T]_0, [PC]_0)}$$

where $[TC]_t$ refers to the concentration of TC at time t, and $[PC]_0$ and $[T]_0$ refer to the initial concentrations of PC and T, respectively. The present disclosure provides a method for tuning this reaction to achieve a desired yield either at equilibrium or at a particular time before equilibrium. Specifically, the initial concentration of P ($[P]_0$) has material impact on both equilibrium and pre-equilibrium yield, such that for reasonably well-designed sequences of P and C, capture yield can be continuously tuned between essentially 0.01% and 99.9%. Below describe several methods for determining the value of $[P]_0$ that results in the desired yield at equilibrium.

(1) In silico determination of $[P]_0$ based on predicted reaction standard free energy ΔG°. The reaction standard free energy can be calculated based on literature parameters or using bioinformatics software, and have been described in detail in WO 2015/094429 A1.

For applications where $[PC]_0 \gg [T]_0$, The value of excess $[P]_0$ needed to achieve equilibrium yield $\chi$ can be analytically calculated as:

$$[P]_0 = e^{-\Delta G^\circ / R\tau} \cdot \frac{1-\chi}{\chi} \cdot ([PC]_0 - \chi[T]_0) - \chi[T]_0$$

Here R represents the gas constant, and $\tau$ represents temperature in Kelvin.

If the initial concentrations further satisfy $[P]_0 \gg [T]_0$, the equation above can be approximated as:

$$[P]_0 \approx e^{-\Delta G^\circ / R\tau} \cdot \frac{1-\chi}{\chi} \cdot [PC]_0$$

When $[T]_0 \gg [PC]_0$, the exact calculation of $[P]_0$ is:

$$[P]_0 = e^{-\Delta G^\circ / R\tau} \cdot \frac{1-\chi}{\chi} \cdot ([T]_0 - \chi[PC]_0) - \chi[PC]_0$$

If the initial concentrations further satisfy $[P]_0 \gg [PC]_0$, the equation above can be approximated as:

$$[P]_0 \approx e^{-\Delta G^\circ / R\tau} \cdot \frac{1-\chi}{\chi} \cdot [T]_0$$

These $[P]_0$ concentrations will give desired yield in an ideal system. In practice, yield may differ significantly from predicted/desired due to errors in predicted $\Delta G^\circ$, probe synthesis errors, target quantitation errors, and unpredictable probe or target interactions in multiplexed settings. Thus, iterative tuning may be necessary or desirable to attain desired yields.

(2) Inferring $[P]_0$ for desired yield based on an experimentally observed yield-$[P]_0$ pair. Experimental data pairing yield with a $[P]_0$ concentration provides more accurate calibration of $\Delta G^\circ$ than in silico predictions based on sequence. Assuming a yield $\chi_1$ is obtained at an initial P concentration $[P]_0$, and the desired yield is $\chi_2$, then the initial P concentration for second round of tuning ($[P]_0'$) can be calculated from the results of the first experiment.

The exact calculation of $[P]_0'$ when $[PC]_0 \gg [T]_0$ is:

$$[P]_0' = \frac{\chi_1}{1-\chi_1} \cdot \frac{[P]_0 + \chi_1[T]_0}{[PC]_0 - \chi_1[T]_0} \cdot \frac{1-\chi_2}{\chi_2} \cdot ([PC]_0 - \chi_2[T]_0) - \chi_2[T]_0$$

and when $[T]_0 \gg [PC]_0$, $[P]_0'$ is calculated as:

$$[P]_0' = \frac{\chi_1}{1-\chi_1} \cdot \frac{[P]_0 + \chi_1[PC]_0}{[T]_0 - \chi_1[PC]_0} \cdot \frac{1-\chi_2}{\chi_2} \cdot ([T]_0 - \chi_2[PC]_0) - \chi_2[PC]_0$$

If the initial concentrations satisfy $[PC]_0 \gg [T]_0$ and $[P]_0 \gg [T]_0$, or $[T]_0 \gg [PC]_0$ and $[P]_0 \gg [PC]_0$, the above 2 equations can both be approximated as Equation 1:

$$[P]_0' \approx \frac{\chi_1}{1-\chi_1} \cdot [P]_0 \cdot \frac{1-\chi_2}{\chi_2}$$

(3) Inferring $[P]_0$ for desired yield based on experimentally observed signal-$[P]_0$ pairs. In some cases, the maximum signal corresponding to 100% yield is difficult to determine, so the yield cannot be calculated accurately. If the initial concentrations satisfy $[PC]_0 \gg [T]_0$ and $[P]_0 \gg [T]_0$, or $[T]_0 \gg [PC]_0$ and $[P]_0 \gg [PC]_0$, a recommended method for stoichiometric tuning is to perform at least 2 experiments with different $[P]_0$ (holding the other concentrations and conditions constant), obtain corresponding background-subtracted signal intensities ($I_s$), and perform a linear fit according to the equation below:

$$\frac{1}{I_s} = k \cdot [P]_0 + b$$

where k and b represent the slope and the intercept respectively. The $[P]_0$ for achieving a particular $I_s$ can be inferred from this linear fit. Note that this method is more accurate at higher yield ($\chi > 10\%$) because the background subtraction may not be accurate.

Figure 2A:
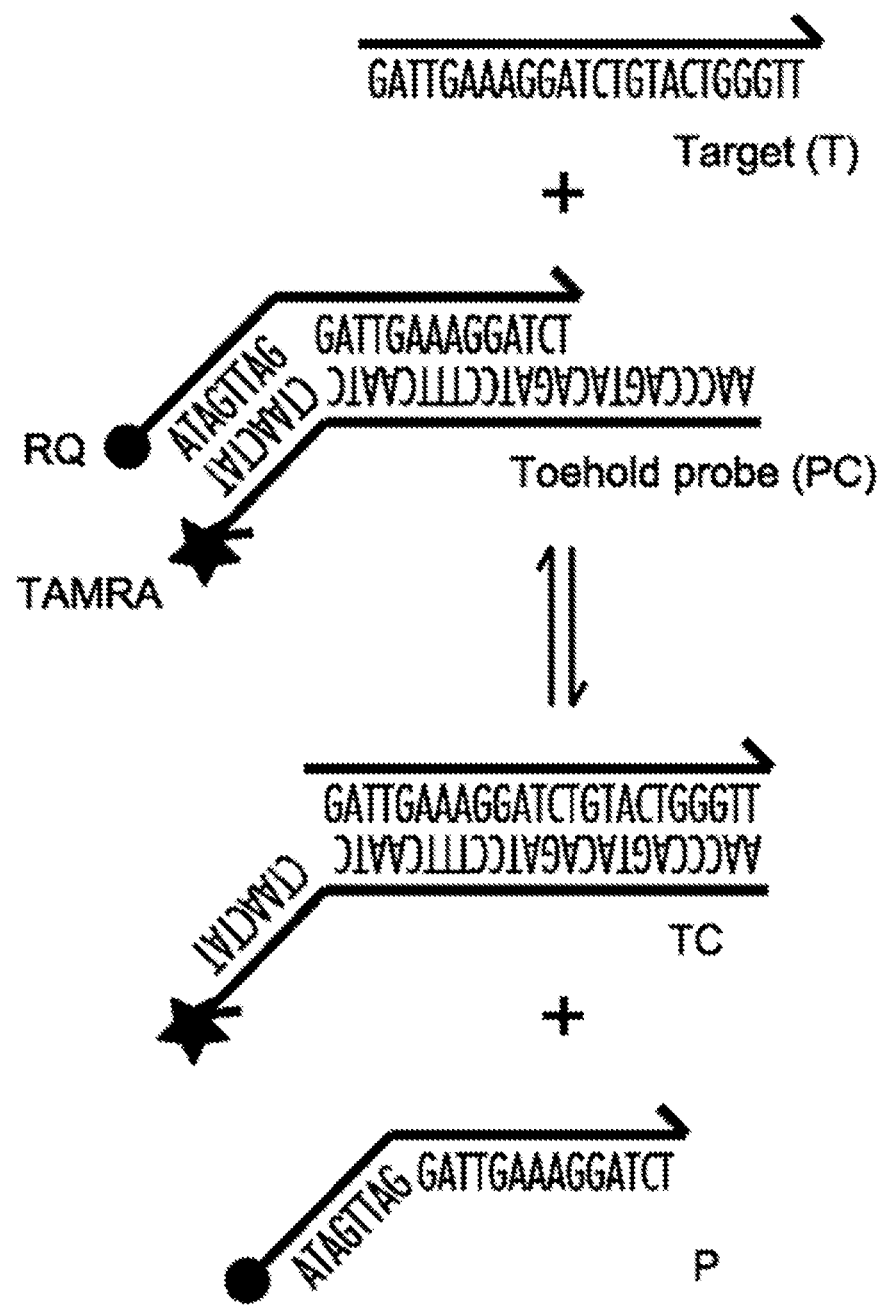
Figure 2B:
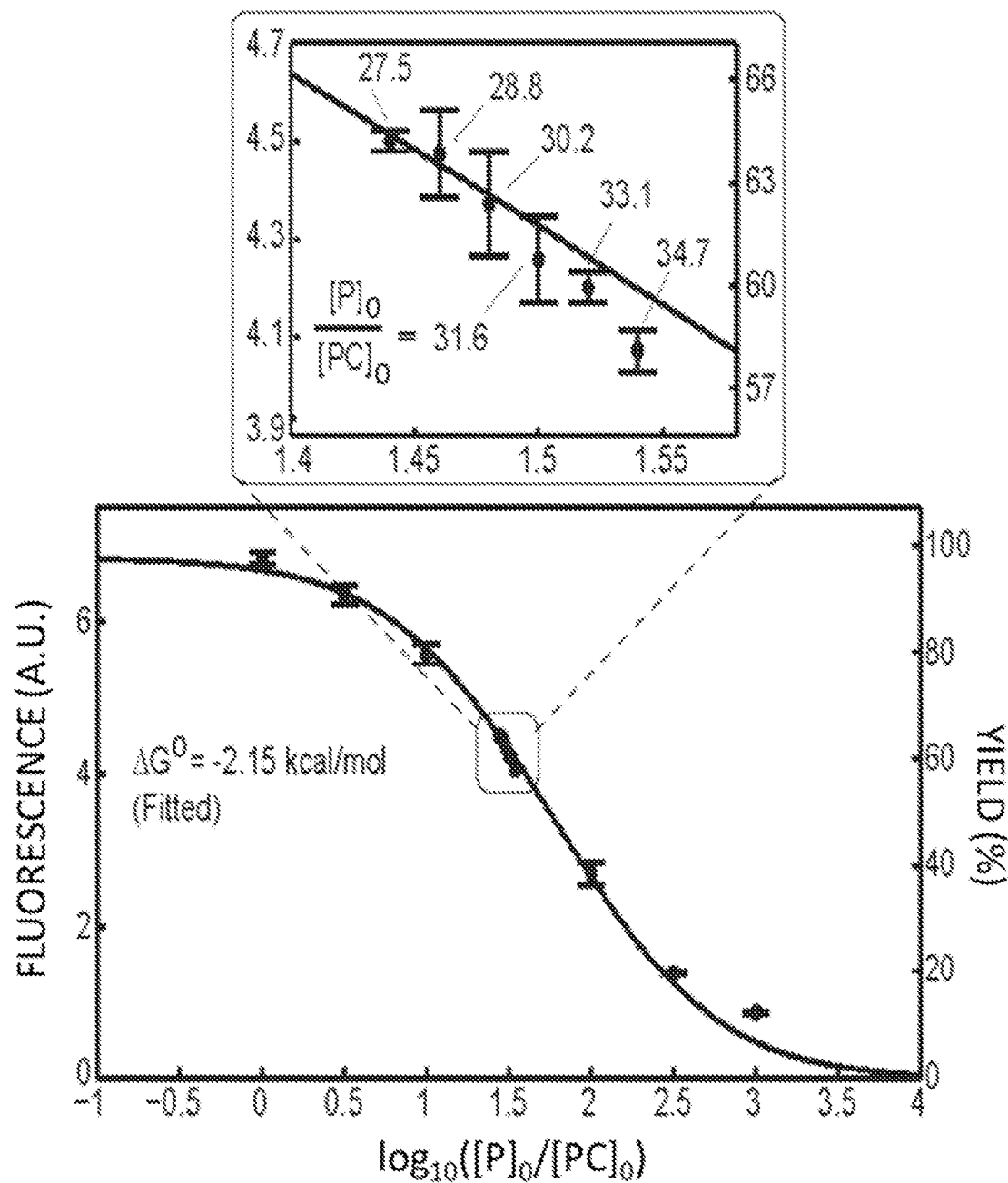

Proof-of-concept validations of the Protector implementation stoichiometric tuning using toehold probes have been performed. The toehold probe is functionalized with a TAMRA fluorophore at 3' end of C, and an Iowa Black RQ quencher at the 5' end of P. P and C are pre-hybridized and form a dark probe. When the target hybridizes to the dark probe, P is displaced, and the fluorescence signal increases (FIG. 2A). Holding $[PC]_0$ and $[T]_0$ constant, we observed the fluorescence of probes with different $[P]_0$, resulting in different yields (FIG. 2B). Target was allowed to react with the probe mixture for 12-24 hours, after which fluorescence is measured. According to our knowledge of kinetics, equilibrium is reached within 4 hours at the experimental conditions. Experimental results were consistent with our analytical predictions.

Figure 3A:
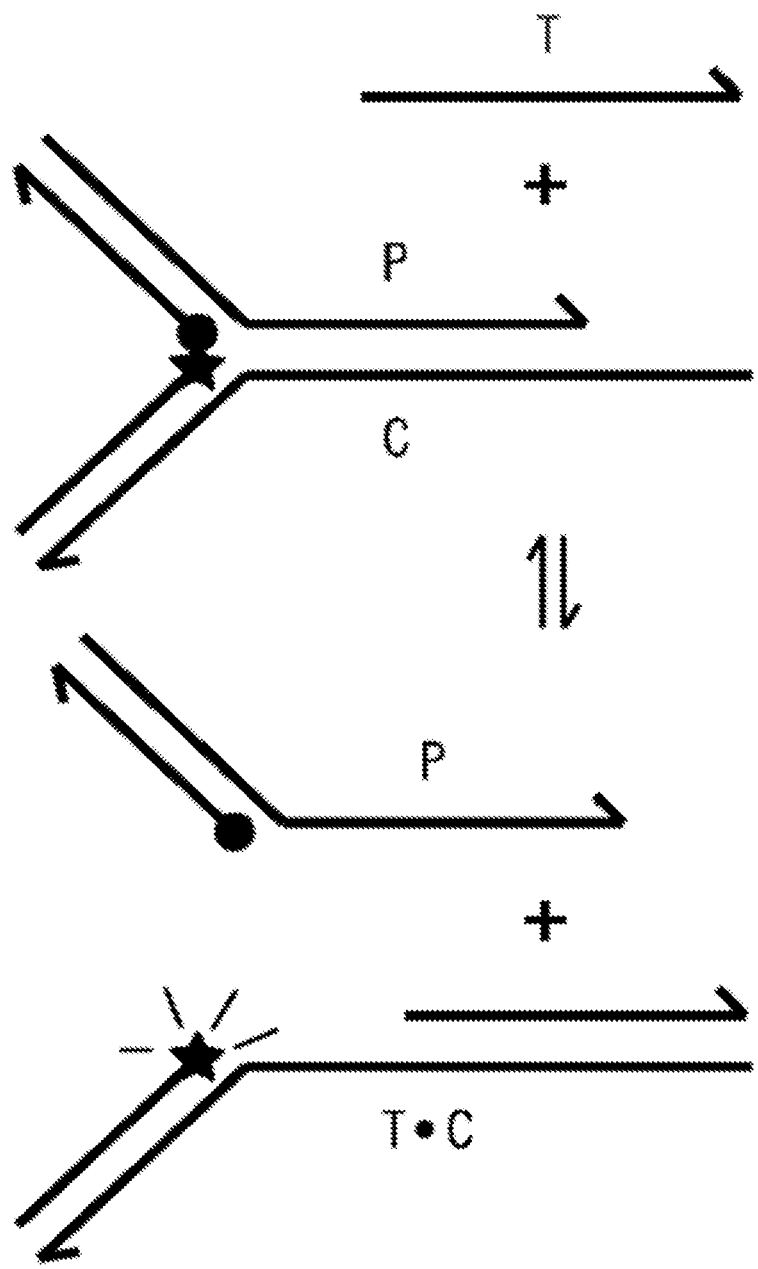
Figure 3B:
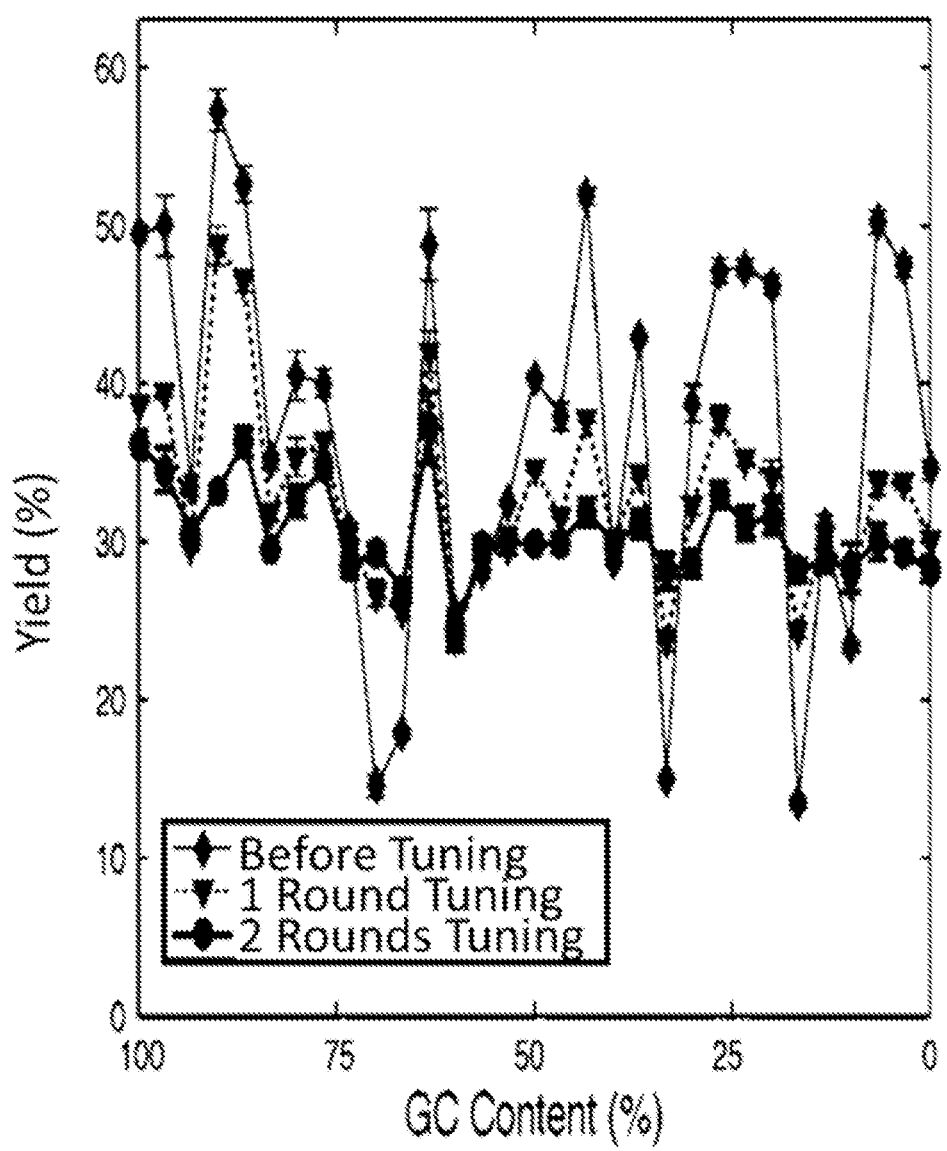

In another embodiment, both P and C can be complexes that comprise 2 or more oligonucleotides formed through Watson-Crick hybridization reactions. An exemplary such PC implementation is illustrated in FIG. 3A, known as an X-Probe. We designed 31 different target sequences with GC content varying uniformly between 0% and 100%. The corresponding X-Probes are designed to achieve $\Delta G^\circ = 0$ kcal/mol, corresponding to roughly 50% yield. Experimentally, we observed that at $[P]_0/[C]_0 = 3$ (FIG. 3B, Before Tuning), yields varied between 57.3% and 13.4%, corresponding to errors in predicted $\Delta G^\circ$. After 2 rounds of stoichiometric tuning by varying the concentration ratio of P and C, we were able to tighten the yield distribution to between 37.2% and 24.0% (FIG. 3B, 2 Rounds Tuning). All the experiments were performed in 5× excess of genomic DNA (100 ng).

Another example application of the PC implementation is SNP discrimination. Many SNP detection methods are based on the differential yields of SNP variants to a probe that specifically targets one variant [ref]. SNP probes exemplify the challenge of balancing yield and selectivity because of the small thermodynamic change ($\Delta\Delta G^\circ$) associated with a single nucleotide mismatch (FIG. 4A). Based on a simple reaction analysis, maximum yield difference ($\Delta\chi$) is achieved when $$[P]_0 \approx e^{-(\Delta G^\circ + \Delta\Delta G^\circ/2)/R\tau} \cdot [T]_0$$

Here the initial concentrations satisfy $[T]_0 > [PC]_0$ and $[P]_0 > [PC]_0$ (FIG. 4B). Because $\Delta\Delta G°$ values vary between +1 and +6 kcal/mol based on sequence, different SNP pairs require different $[P]_0$ for optimal discrimination. FIG. 4C shows the fluorescence signal produced by a toehold probe when reacted with its DNA target and 11 SNPs. Based on these results, we calculated the $\Delta G°$ of the toehold probe with the intended target and each SNP, from which we numerically calculated the $\Delta\Delta G°$ of each SNP pair. From this, we calculated the $[P]_0$ needed for each individual SNP, and the experimental results on the stoichiometrically tuned probes for each SNP pair are shown in FIG. 4D. The range of yield difference was improved from 17.2-83.3% to 47.0-88.6%.

Blocker Implementation:

The second implementation, or the Blocker implementation, involves a probe nucleic acid molecule (denoted as D) comprising a first and a second subsequence that are complementary to adjacent subsequences of the target, and an auxiliary nucleic acid molecule (denoted as the Blocker or B) comprising a third subsequence that is homologous to the second subsequence but not the first subsequence; B has higher initial concentration than D. In some embodiments, B further comprises a fourth subsequence that is complementary to the target sequence and not homologous to the first or the second subsequence. In some embodiments, B and D are each an oligonucleotide; an example of this embodiment is illustrated in FIG. 1B.

The sequence design of B and D, relative to a target sequence T, are such that the preponderance of B and D molecules are mutually exclusive in hybridization to T, with only a small concentration of trimolecular intermediate species TBD existing at any given point of time. Additionally, B and D are both designed to bind stably to T, with only a small concentration of free T existing at any given point of time when the sum of the concentrations of B and D exceed that of T. When these assumptions are met, the system can be simply expressed by the chemical reaction D+TB≈TD+B. The yield of this reaction at a given time t is defined as $\chi_t = [TD]_t/[T]_0$, where $[TD]_t$ refers to the concentration of TD at time t. Similar to the Protector implementation, there are 3 different methods for stoichiometric tuning to a desired equilibrium yield.

(1) In silico determination of $[B]_0$ based on predicted reaction standard free energy $\Delta G°$. The initial concentration of B ($[B]_0$) needed for achieving a particular yield χ can be calculated from the predicted $\Delta G°$ of reaction D+TB≈TD+B. The equation for exact calculation of $[B]_0$ is:

$$[B]_0 = e^{-\Delta G°/Rr} \cdot \frac{1-x}{x} \cdot ([D]_0 - x[T]_0) - x[T]_0 + [T]_0$$

When the initial concentrations further satisfy $[B]_0 > 2[T]_0$, the equation above can be approximated as:

$$[B]_0 \approx e^{-\Delta G°/Rr} \cdot \frac{1-x}{x} \cdot [D]_0$$

(2) Inferring $[B]_0$ for desired yield based on an experimentally observed yield-$[B]_0$ pair. If an initial B concentration $[B]_0$ produces a yield $\chi_1$, then the initial B concentration ($[B]_0'$) needed to achieve yield $\chi_2$ is:

$$[B]_0' = \frac{x_1}{1-x_1} \cdot \frac{[B]_0 - [T]_0 + x_1[T]_0}{[D]_0 - x_1[T]_0} \cdot \frac{1-x_2}{x_2} \cdot ([D]_0 - x_2[T]_0) + [T]_0 - x_2[T]_0$$

If $[B]_0 > 2[T]_0$, the equation above can be approximated as Equation 2:

$$[B]_0' \approx \frac{x_1}{1-x_1} \cdot [B]_0 \cdot \frac{1-x_2}{x_2}$$

(3) Inferring $[B]_0$ for desired yield based on experimentally observed signal-$[B]_0$ pairs. In some cases, the maximum signal corresponding to 100% yield is difficult to determine, so the yield cannot be calculated accurately. If $[B]_0 > 2[T]_0$, $[B]_0$ and the signal intensity $I_s$ approximately satisfy:

$$\frac{1}{I_s} = k \cdot [B]_0 + b$$

So a linear fit can be applied to the obtained experimental data (at least 2 different $[B]_0$), and the $[B]_0$ for achieving desired $I_s$ can be inferred from the linear fit.

To validate the Blocker implementation, we used a target that is functionalized with TAMRA at 3' end, and a Displacer functionalized with Iowa Black RQ at the 5' end. Hybridization of T and D results in a decrease of fluorescence signal, so the maximum signal indicates 0% yield, and the background signal indicates 100% yield (FIG. 5A). We observed the fluorescence at different $[B]_0$, $[D]_0$ and $[T]_0$ were held constant (FIG. 5B). T, B, and D are mixed together and incubated for 12-24 hours before measuring fluorescence. The experimental results were consistent with analytical predictions. Note that stoichiometric tuning does not need the target to be functionalized; this specific modification is for demonstration purpose only.

In the typical embodiments shown above, the probe (C or D) and the auxiliary species (P or B) are all single-stranded. In other embodiments, any of these molecules may comprise additional pre-hybridized oligonucleotides for ease of attaching chemical modifications, capture, or controlling kinetics/thermodynamics.

In FIGS. 6A and C, one of the molecules is partially double-stranded, and the two oligonucleotides in this molecule are hybridized via a region that is not homologous to the target. FIG. 6B shows a typical X-probe structure in which both P and C comprise 2 oligonucleotides, such that the sequences of fluorophore-modified and quencher-modified strands are decoupled from the target sequence. FIG. 6D shows a special case where B further comprises a complementary oligonucleotide that dissociates when B hybridizes to the target; this may be used for highly-structured sequences to improve reaction kinetics.

Pre-Equilibrium Stoichiometric Tuning:

In some assay conditions, equilibrium is not achievable due to long incubation time, reagent instability, or sample degradation. We performed ODE simulations and show that stoichiometric tuning can also be used achieve a subset of desired yields at pre-equilibrium conditions.

For Protector implementation, the ODE simulation was based on the reaction:

$$T + PC \underset{k_r}{\overset{k_f}{\rightleftharpoons}} TC + P$$

and the simulation results are shown in FIGS. 7A-7C. Assuming $[PC]_0 \gg [T]_0$ and $[P]_0 \gg [T]_0$, the yield at a particular reaction time ($\chi_t$) can be approximately calculated as:

$$\chi_t = \chi_\infty (1 - e^{-k_f t \cdot [PC]_0 / \chi_\infty})$$

where $\chi_\infty$ denotes the equilibrium yield, $k_f$ denotes the rate constant of forward reaction, and t denotes reaction time. At pre-equilibrium conditions, the maximum yield achievable is lower than 100%, and it can be approximately calculated as:

$$\chi_{t,max} = 1 - e^{-k_f t \cdot [PC]_0}$$

It can be derived from the equations above that the criterion $k_f t \cdot [PC]_0 \chi_\infty$ indicates that the pre-equilibrium condition "resists" stoichiometric tuning, i.e. yield almost remains constant when $[P]_0$ is changed. To ensure that stoichiometric tuning is applicable, reaction time t and $[PC]_0$ need to satisfy $k_f t \cdot [PC]_0 > 1$ (FIG. 7B). In this case, stoichiometric tuning can be calculated similarly to equilibrium tuning method (3): $[P]_0$ needed for achieving a particular background-subtracted signal intensity $I_s$ can be inferred from the linear fit (FIG. 7C):

$$\frac{1}{I_s} = k \cdot [P]_0 + b$$

At least 2 data points (2 different $[P]_0$ and corresponding $I_s$ or $\chi_t$) are needed to obtain k and b values.

For the Blocker implementation, the ODE simulation was based on the reactions:

$$T + B \underset{k_{r1}}{\overset{k_{f1}}{\rightleftharpoons}} TB$$

$$T + D \underset{k_{r2}}{\overset{k_{f2}}{\rightleftharpoons}} TD$$

$$TB + D \underset{k_{r3}}{\overset{k_{f3}}{\rightleftharpoons}} TD + B$$

and the results shown in FIGS. 8A-8C indicates that some pre-equilibrium conditions can be tuned using a linear fit similar to equilibrium tuning method.

Stoichiometric tuning can be more difficult at pre-equilibrium conditions and highly-multiplexed settings. Kinetics of oligonucleotide strand displacement and hybridization reactions are not as well understood as their thermodynamics, so prediction of $k_f$ is still not accurate enough. Highly-multiplexed settings at equilibrium or pre-equilibrium may involve unexpected interactions leading to yield change. In these cases, iterative tuning based on previous observed yield or signal is recommended. Calculation methods (2) and (3) can be applied to iterative tuning.

Unless explicitly stated otherwise, "complementary" in this document refers to "partially or fully complementary".

A nucleic acid molecule is complementary to another if the nucleotides of each can simultaneously form several Watson-Crick base pairs with each other. In this context, complementary can mean fully and/or partially complementary and can include mismatched base pairs. In some aspects, the present disclosure provides for minor sequence differences between nucleic acid molecule subsequences. For example, in the PC implementation, the first probe subsequence of the first nucleic acid molecule and the second probe subsequence of the first nucleic acid molecule can be complementary to a first target subsequence and a second target subsequence, respectively. However, mismatches can be present between the first and second target subsequences and the first and second probe subsequences, respectively, while still maintaining complementarity. FIG. 4C depicts an example of such complementarity despite mismatches. Thus, to the extent that the probes can form several Watson-Crick base pairs with the target, the resulting probes maintain consistency with the principles of probe construction described herein.

In an embodiment, a method for providing a nucleic acid probe for selective capture or enrichment of a nucleic acid molecule bearing a target nucleic acid sequence with a desired yield is provided, the method comprising contacting a first sample containing the nucleic acid molecule bearing the target nucleic acid sequence with a test solution comprising the nucleic acid probe at a temperature and a buffer condition conducive to hybridization of the target nucleic acid sequence to the nucleic acid probe. The nucleic acid probe includes a first nucleic acid molecule and a second nucleic acid molecule. The first and second nucleic acid molecules are present in the nucleic acid probe at a first concentration and a second concentration, respectively, and the second concentration is greater than the first concentration. The first nucleic acid sequence includes a first probe subsequence and a second probe subsequence which are complementary to a first target subsequence and a second target subsequence of the nucleic acid molecule, respectively. The second nucleic acid sequence includes a third probe subsequence that is complementary to at least a subsequence of the first probe subsequence. The method then includes a step for determining an experimental yield, the experimental yield being the proportion of the target nucleic acid sequence that is hybridized to the first nucleic acid molecule. Once the experimental yield is determined, a third concentration $[P]'_0$ of the second nucleic acid molecule is determined according to Equation 1, where $[P]_0$ is the second concentration, $\chi_1$ is the experimental yield and $\chi_2$ is the desired yield which is the desired proportion of the target nucleic acid sequence that is hybridized to the first nucleic acid molecule. Once the third concentration is determined, the method further includes the step of providing instructions to use the third concentration of the second nucleic acid molecule for preparation of the nucleic acid probe or preparing the nucleic acid probe with the second nucleic acid molecule at the third concentration.

In certain aspects of the foregoing embodiment, the first nucleic acid can further include a fourth probe subsequence that is not complementary to the target nucleic acid sequence nor is complementary to any sequence on the nucleic acid molecule within 30 nucleotides of the target nucleic acid sequence, and the second nucleic acid molecule can further include a fifth probe subsequence that is at least 80% complementary to the fourth probe subsequence. In certain aspects of the foregoing embodiment, the second concentration in the nucleic acid probes can be between 1.1 and 10,000 times the first concentration.

In another embodiment, a method for providing a nucleic acid probe for selective capture or enrichment of a nucleic acid molecule bearing a target nucleic acid sequence with a desired yield is provided, the method comprising contacting a first sample containing the nucleic acid molecule bearing the target nucleic acid sequence with a test solution comprising the nucleic acid probe at a temperature and a buffer condition conducive to hybridization of the target nucleic acid sequence to the nucleic acid probe. The nucleic acid probe includes the first nucleic acid molecule and a second nucleic acid molecule. The first and second nucleic acid molecules are present in the nucleic acid probe at a first concentration and a second concentration, respectively. The first nucleic acid sequence includes a first probe subsequence and a second probe subsequence which are complementary to a first target subsequence and a second target subsequence of the nucleic acid molecule, respectively. The first target subsequence includes at least a portion of the target nucleic acid sequence. The second nucleic acid sequence includes a third probe subsequence that is complementary to the first target subsequence. The second nucleic acid molecule does not contain a subsequence that is complementary to the second target subsequence. The method then includes a step for determining an experimental yield, the experimental yield being the proportion of the target nucleic acid sequence that is hybridized to the first nucleic acid molecule. Once the experimental yield is determined, a third concentration $[B]'_0$ of the second nucleic acid molecule is determined according to Equation 2, where $[B]_0$ is the second concentration, $\chi_1$ is the experimental yield and $\chi_2$ is the desired yield which is the desired proportion of the target nucleic acid sequence that is hybridized to the first nucleic acid molecule. Once the third concentration is determined, the method further includes the step of providing instructions to use the third concentration of the second nucleic acid molecule for preparation of the nucleic acid probe or preparing the nucleic acid probe with the second nucleic acid molecule at the third concentration.

In certain aspects of the foregoing embodiment, the second nucleic acid can further include a fourth probe subsequence that is complementary to a third target subsequence of the nucleic acid molecule, wherein the third target subsequence is separate from the first and second target subsequence and within 30 nucleotides of the first or second target subsequences. In certain aspects of the foregoing embodiment, the second concentration in the nucleic acid probes can be between 0.001 and 1,000 times the first concentration.

In certain aspects, the first nucleic acid molecules of the nucleic acid probes of the foregoing embodiments can comprise, by way of example but not limitation, a DNA oligonucleotide, deoxyuridines, RNA nucleotides, or a photocleavable linker moiety. In some aspects of the foregoing embodiments, the first nucleic acid molecule is a DNA oligonucleotide. In certain aspects of the foregoing embodiments, the second nucleic acid molecule of the nucleic acid probes is a DNA oligonucleotide.

In some instances of the foregoing embodiments, the first nucleic acid molecule of the nucleic acid probes can further comprise a functional moiety capable of interacting with a binding partner. In such instances, the step of determining the experimental yield can be performed by capturing the first nucleic acid molecule through interaction of the functional moiety and binding partner.

In some embodiments, the foregoing methods can further include, prior to determining the experimental yield, capturing nucleic acid molecules hybridized to the first nucleic acid molecule through solid-phase separation. In some embodiments, the foregoing methods can further include, prior to determining the experimental yield, selectively degrading the first nucleic acid molecule after capturing through solid-phase separation. In some instances, the selective degradation of the first nucleic acid can be through a nuclease. In some aspects, the first nucleic acid molecule can include a photocleavable linker moiety. In some instances, where the first nucleic acid molecule comprises a photocleavable linker moiety, the selective degradation of the first nucleic acid is through illumination by light of a wavelength sufficient to cleave the photocleavable linker moiety.

In some aspects of the foregoing embodiments, a method for selective capture or enrichment of a nucleic acid molecule bearing a target nucleic acid sequence with a desired yield comprises contacting a sample containing the nucleic acid molecule bearing the target nucleic acid sequence with the nucleic acid probe of any of the foregoing embodiments.

In still another embodiment, a nucleic acid probe composition for selectively capturing or enriching a nucleic acid molecule bearing a target nucleic acid sequence is provided. The nucleic acid probe composition includes a first nucleic acid molecule and a second nucleic acid molecule at a first concentration and a second concentration, respectively. The first nucleic acid molecule includes a first probe subsequence that is complementary to a first target subsequence of the nucleic acid molecule and a second probe subsequence that is complementary to a second target subsequence of the nucleic acid molecule. The first target subsequence includes at least a portion of the target nucleic acid sequence. The second nucleic acid molecule includes a third probe subsequence and a fourth probe subsequence. The third probe subsequence is complementary to the first target subsequence or a subsequence contained within the first target subsequence. The fourth probe subsequence is complementary to a third target subsequence that is separate from the first and second target subsequences, but is within 30 nucleotides of the first or second target subsequences.

In the foregoing embodiment, the first nucleic acid molecule can further comprises a functional moiety capable of interacting with a binding partner. In some aspects, the second concentration is between 0.001 and 1,000 times the first concentration. The first and/or second nucleic acid molecules can be DNA oligonucleotides. The first nucleic acid molecule can also include deoxyuridines, RNA nucleotides, or a photocleavable linker moiety.

What is claimed is:

1. A method for providing or preparing a nucleic acid probe for selective capture or enrichment of a nucleic acid molecule bearing a target nucleic acid sequence with a desired yield, comprising in order:
   contacting a first sample containing the nucleic acid molecule bearing the target nucleic acid sequence with a test solution comprising the nucleic acid probe comprising a first concentration of a first nucleic acid molecule and a second concentration of a second nucleic acid molecule at a temperature and a buffer condition conducive to hybridization of the target nucleic acid sequence to the first nucleic acid molecule, wherein the second concentration is greater than the first concentration, wherein the first nucleic acid molecule comprises a first probe subsequence and a second probe subsequence, wherein the first probe subsequence is complementary to and sufficient to hybridize to a first target subsequence of the nucleic acid molecule and the second probe subsequence is complementary to and sufficient to hybridize to a second target subsequence of the nucleic acid molecule, wherein at least a portion of the target nucleic acid sequence is contained within the first target subsequence, and wherein the second nucleic acid molecule comprises a third probe subsequence that is complementary to and sufficient to hybridize at least a subsequence of the first probe subsequence and is not sufficient to hybridize to the second probe subsequence;
   determining an experimental yield, wherein the experimental yield is the proportion of the target nucleic acid sequence in the first sample that is hybridized to the first nucleic acid molecule;
   determining a third concentration of the second nucleic acid molecule, wherein the third concentration $[P]'_0$ is determined by Equation 1, wherein $[P]_0$ is the second concentration, wherein $\chi_1$ is the experimental yield, and wherein $\chi_2$ is the desired yield, wherein the desired yield is the desired proportion of the target nucleic acid sequence that is hybridized to the first nucleic acid molecule; and
   providing instructions to use the first concentration of the first nucleic acid molecule and the third concentration of the second nucleic acid molecule for preparation of the nucleic acid probe or preparing the nucleic acid probe with the first nucleic acid molecule at the first concentration and the second nucleic acid molecule at the third concentration.

2. The method of claim 1, wherein the first nucleic acid molecule is a DNA oligonucleotide.

3. The method of claim 1, wherein the first nucleic acid molecule comprises deoxyuridines, RNA nucleotides, or a photocleavable linker moiety.

4. The method of claim 1, wherein the second nucleic acid molecule is a DNA oligonucleotide.

5. The method of claim 1, wherein the second concentration is between 1.1 and 10,000 times the first concentration.

6. The method of claim 1, wherein the first nucleic acid molecule further comprises a functional moiety capable of interacting with a binding partner, wherein the step of determining the experimental yield is performed by capturing the first nucleic acid molecule through interaction of the functional moiety and binding partner.

7. The method of claim 1 wherein prior to determining the experimental yield, capturing nucleic acid molecules hybridized to the first nucleic acid molecule through solid-phase separation.

8. The method of claim 7 wherein prior to determining the experimental yield, selectively degrading the first nucleic acid molecule after capturing through solid-phase separation.

9. The method of claim 8, wherein the selective degradation of the first nucleic acid molecule is through a nuclease.

10. The method of claim 8 wherein the first nucleic acid molecule comprises a photocleavable linker moiety.

11. The method of claim 10, wherein the selective degradation of the first nucleic acid molecule is through illumination by light of a wavelength sufficient to cleave the photocleavable linker moiety.

12. The method of claim 1, further comprising contacting a second sample containing the nucleic acid molecule bearing the target nucleic acid sequence with a second test solution comprising a second nucleic acid probe comprising the first nucleic acid molecule at the first concentration and the second nucleic acid molecule at the third concentration at a temperature and a buffer condition conducive to hybridization of the target nucleic acid sequence to the first nucleic acid molecule.

13. A method for preparing a nucleic acid probe for selective capture or enrichment of a nucleic acid molecule bearing a target nucleic acid sequence with a desired yield, comprising in order:

contacting a first sample containing the nucleic acid molecule bearing the target nucleic acid sequence with a test solution comprising the nucleic acid probe comprising a first concentration of a first nucleic acid molecule and a second concentration of a second nucleic acid molecule at a temperature and a buffer condition conducive to hybridization of the target nucleic acid sequence to the first nucleic acid molecule, wherein the second concentration is greater than the first concentration, wherein the first nucleic acid molecule comprises a first probe subsequence and a second probe subsequence, wherein the first probe subsequence is complementary to and sufficient to hybridize to a first target subsequence of the nucleic acid molecule and the second probe subsequence is complementary to and sufficient to hybridize to a second target subsequence of the nucleic acid molecule, wherein at least a portion of the target nucleic acid sequence is contained within the first target subsequence, and wherein the second nucleic acid molecule comprises a third probe subsequence that is complementary to and sufficient to hybridize to at least a subsequence of the first probe subsequence and is not sufficient to hybridize to the second probe subsequence;

determining an experimental yield, wherein the experimental yield is the proportion of the target nucleic acid sequence in the first sample that is hybridized to the first nucleic acid molecule;

determining a third concentration of the second nucleic acid molecule, wherein the third concentration $[P]'_0$ is determined by Equation 1, wherein $[P]_0$ is the second concentration, wherein $\chi_1$ is the experimental yield, and wherein $\chi_2$ is the desired yield, wherein the desired yield is the desired proportion of the target nucleic acid sequence that is hybridized to the first nucleic acid molecule; and preparing the nucleic acid probe by combining the first concentration of the first nucleic acid molecule with the third concentration of the second nucleic acid molecule.

14. A method for selective capture or enrichment of a nucleic acid molecule bearing a target nucleic acid sequence with a desired yield, the method comprising contacting a sample containing the nucleic acid molecule bearing the target nucleic acid sequence with the nucleic acid probe prepared in claim 13.

\* \* \* \* \*

SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
gattgaaagg atctgtactg ggtt                                              24

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atagttagga ttgaaaggat ct                                                22

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aacccagtac agatcctttc aatcctaact at                                     32

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 ggcgccccc gccggccccg ccgccgccgc                                         30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttataaaaaa taattaaaat aataataata                                        30

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgrtytktg ygttraaawg gtrttytatr gtawttasga a                           41

<210> SEQ ID NO 7
<211> LENGTH: 31
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 7
ctgctggaag gacttgaggg actcccttac t                                    31

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagtccctca agtccttcca gcag                                            24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agtaagggag tccctcaagt ccttc                                           25
```